United States Patent

Malabarba et al.

Patent Number: 5,684,127
Date of Patent: Nov. 4, 1997

[54] TETRAPEPTIDES DERIVING FROM DALBAHEPTIDE ANTIBIOTICS

[75] Inventors: Adriano Malabarba, Binasco; Romeo Ciabatti, Novate Milanese, both of Italy

[73] Assignee: Gruppo Lepetit SpA, Milan, Italy

[21] Appl. No.: 468,732

[22] Filed: Jun. 6, 1995

Related U.S. Application Data

[62] Division of Ser. No. 391,378, Feb. 17, 1995, which is a continuation of Ser. No. 70,472, which is a continuaiton-in-part of PCT/EP91/02250, Nov. 28, 1991, abandoned.

[51] Int. Cl.$^6$ .............................. C07K 1/02; C07K 5/10; C07K 5/12; A61K 38/07
[52] U.S. Cl. .......................... 530/317; 530/322; 530/330; 530/333; 514/9; 514/11
[58] Field of Search .................... 514/9, 11; 530/330, 530/333, 317, 322

[56] References Cited

FOREIGN PATENT DOCUMENTS 409045  1/1991  European Pat. Off. .

OTHER PUBLICATIONS

Mcgahren et al., 'Structure of Avoparcin componets', Journal of the American Chemical Society, vol. 102, No. 5, pp. 1671–1684, Feb. 27, 1980.

*Primary Examiner*—Cecilia J. Tsang
*Assistant Examiner*—Anish Gupta
*Attorney, Agent, or Firm*—J. Michael Dixon

[57] ABSTRACT

Tetrapeptides of general formula (I) deriving from dalbaheptide antibiotics

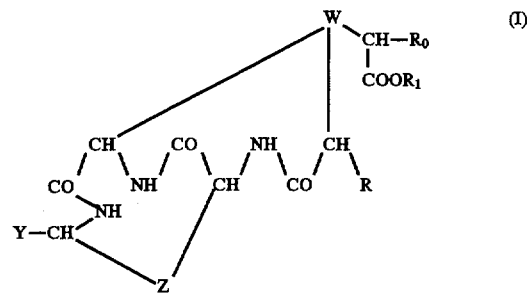

wherein:

W and Z represent the relative portions of the aglycon of an antibiotic of the dalbaheptide group (aglucodalbaheptides);

Y represents a carboxylic group or a functional derivative of said carboxylic group;

R and $R_0$ each independently represent amino or a protected amino group;

$R_1$ represents hydrogen or a protecting group of the carboxylic function;

and its salts with acids and bases as well as its inner salts.

A process for producing the tetrapeptides of formula (I) from the corresponding dalbaheptides and aglucodalbaheptides.

2 Claims, No Drawings

TETRAPEPTIDES DERIVING FROM DALBAHEPTIDE ANTIBIOTICS

This a Division of application Ser. No. 08/391,378, filed Feb. 17, 1995 which is a continuation of application Ser. No. 08/070,472, filed Jun. 3, 1993, now abandoned.

This is a continuation-in-part of International Patent Application No. PCT/EP91/02250 designating the United States of America and having International filing date of Nov. 28, 1991.

This invention concerns tetrapeptides of general formula (I) deriving from dalbaheptide antibiotics

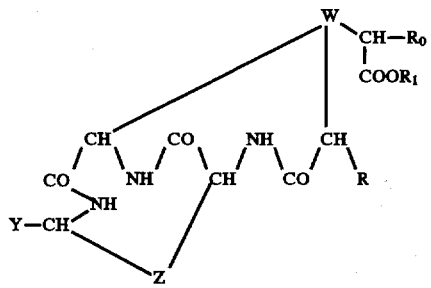

wherein:
- W and Z represent the relative portions of the aglycon of an antibiotic of the dalbaheptide group (aglucodalbaheptides);
- Y represents a carboxylic group or a functional derivative of said carboxylic group;
- R and $R_0$ each independently represent amino or a protected amino group;
- and $R_1$ is hydrogen or a protecting group of the carboxylic function.

The invention includes the salts of the above represented tetrapeptides with acids or bases as well as their inner salts.

A further object of this invention is a process for producing the tetrapeptides of formula (I) above from the corresponding dalbaheptides and aglucodalbaheptides, that is, the dalbaheptides wherein any sugar unit is removed.

With the term dalbaheptide are defined all antibiotic substances having in common a highly modified linear heptapeptidic structure made up of seven amino acids, five of which are constantly aryl- and arylmethyl-amino acids, said structure being determinant of a common mechanism of action, i.e. the specific complexation with the D-alanyl-D-alanine terminus of one or more intermediates of the cell wall synthesis which leads to cell disruption (see also: F. Parenti and B. Cavalleri, "Novel glycopeptide antibiotics of the dalbaheptide group", Drugs of the future, Vol. 15 (1): 57–72 (1990) and B. Cavalleri, F. Parenti: "Glycopeptides (dalbaheptides)", in Kirk-Othmer's Encyclopedia of Chemical Technology, Vol. 2, 995–1018, J. Wiley & Sons, 1992)).

The dalbaheptide antibiotics can be conventionally represented by the following general structure formula (II)

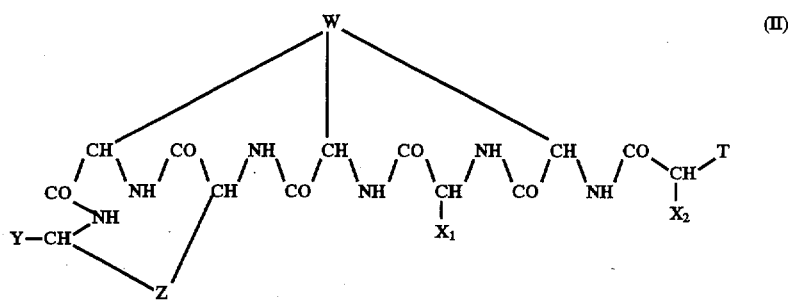

wherein:
- W, Z, $X_1$, $X_2$ and T represent the relative portions of an antibiotic of the dalbaheptide group;
- and Y represents a carboxylic group or a functional derivative thereof.

The formula (II) includes the salts of dalbaheptide antibiotics with acids and bases as well as their inner salts.

In the general structure represented by the formula (II), the above mentioned five fundamental aryl- and arylmethyl-amino acids are those connected with the rests Z and W. Apart from slight differences in the substitutions on the respective aryl portion, the five aryl- and arylmethyl-amino acids are substantially common to all members of the dalbaheptide antibiotics group, while the different type and structure of the two remaining amino acid portions which bear the substituents $X_1$ and $X_2$ allow a further classification of the dalbaheptides so far known into four different subgroups, each of which is referred, for practical reasons, to a well known antibiotic of the group that, in the previous scientific literature, has been generally identified as glycopeptide antibiotics.

Said four sub-groups can be defined respectively as ristocetin-type, vancomycin-type, avoparcin-type and synmonicin-type antibiotics.

This classification is not limiting the scope of this invention but it is useful for the purpose of a more precise description of this invention.

According to the terms and definitions of this specification, the dalbaheptide antibiotics as well as the four sub-groups into which they are presently classified, include both products produced as metabolites of microbial strains, as well as semisynthetic derivatives thereof. The fermentation products generally bear sugar moieties conjugated with the hydroxy groups positioned on the aryl or arylmethyl portions of the five fundamental amino acids, or on the $X_1$ and/or $X_2$ moieties when they contain hydroxylated aromatic ring moieties. In a few cases, one phenolic hydroxy function may be esterified with a sulfuric acid rest. In the fermentation products the function represented by the symbol Y generally is a carboxylic or a lower alkyl carboxyester, while the symbol T, in general, represents an amino or a lower alkyl amino (e.g. methylamino) rest.

In the dalbaheptides literature are reported also compounds wherein T represents a di-(lower alkyl)amino group (e.g. orienticin D, chloroorienticin C, D, E), or a trimethylammonio group whose positive charge is neutralized by a carboxylate anion formed by the carboxylic group represented by the symbol Y (e.g. antibiotic M43A, B and C). However, these dalbaheptides (and the respective aglycons)

cannot be useful as direct precursors of the tetrapepetide of formula (I) according to the process of this invention.

The semisynthetic derivatives described in the patents and scientific literature are, for instance, products deriving from complete or partial hydrolysis of the sugar portions, thus having free hydroxy groups on the aryl or the arylmethyl portions, products deriving from the elimination of the benzylic hydroxy group on the arylmethyl portions, products deriving from the introduction of specific sugar moieties or aliphatic or alicyclic rests on a phenolic hydroxy function, products deriving from the modifications of the carboxylic moiety Y to form functional derivatives thereof, e.g. esters, amide or hydrazide derivatives or products deriving from the modification of the portion T yielding variously substituted amino groups (e.g. by alkylation or acylation) or resulting from the introduction of protecting groups of said aminic function or products deriving from the acylation of the aminic rests of the amino sugar moieties, or products resulting from the dehalogenation of the aryl moieties originally containing halo substituents or products deriving from the introduction of halo (preferably chloro, bromo and jodo) substituents on the aryl moieties. Said semisynthetic derivatives may contain more than one of the above mentioned modifications of the basic structure of the natural products.

A more complete detailed description of the dalbaheptide antibiotics is given in the European Patent Application Publication No. 409045 which indicates the appropriate references to identify a large number of members of this class of compounds and their method of obtainment.

For the purpose of a more detailed description of this invention the tetrapeptides of formula (I) can be formally identified as compounds deriving from the aglycons of the dalbaheptide antibiotics. In fact, although for the manufacture of the tetrapeptides of formula (I) both the glycosylated dalbahpetides and the corresponding pseudoaglycons and aglycons may be utilized as starting materials, for the purpose of clarity and semplicity in this description and claims, it will be made reference to aglucodalbaheptides as the formal precursors of the tetrapeptides of formula (I) since the final compounds and most of the intermediates of their manufacture process do not contain the typical sugar unit(s) of the original dalbaheptides.

By following the same method utilized above for the description of the dalbaheptide antibiotics, the aglycons of the dalbaheptide antibiotics (aglucodalbaheptides) which are the formal precursors of the tetrapepetides of this invention can be represented conventionally with the following general structure (IIa)

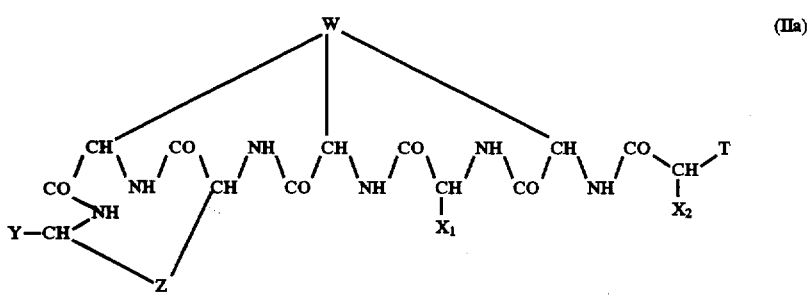

(IIa)

wherein:

W, Z, $X_1$, and $X_2$ represent the relative portions of the aglycon of an antibiotic of the dalbaheptide group;

T represents amino, alkylamino or a protected amino group from which the original amino group can be readily restored;

and Y represents a carboxylic group or a functional derivative thereof.

The formula (IIa) includes the salts of aglucodalbaheptide antibiotics with acids and bases as well as their inner salts.
According to this invention, the tetrapeptides of general formula (I) can be obtained from the above mentioned aglucodalbaheptide precursors of general formula (IIa) through a series of reaction steps (see Reaction Schemes 1 and 2).
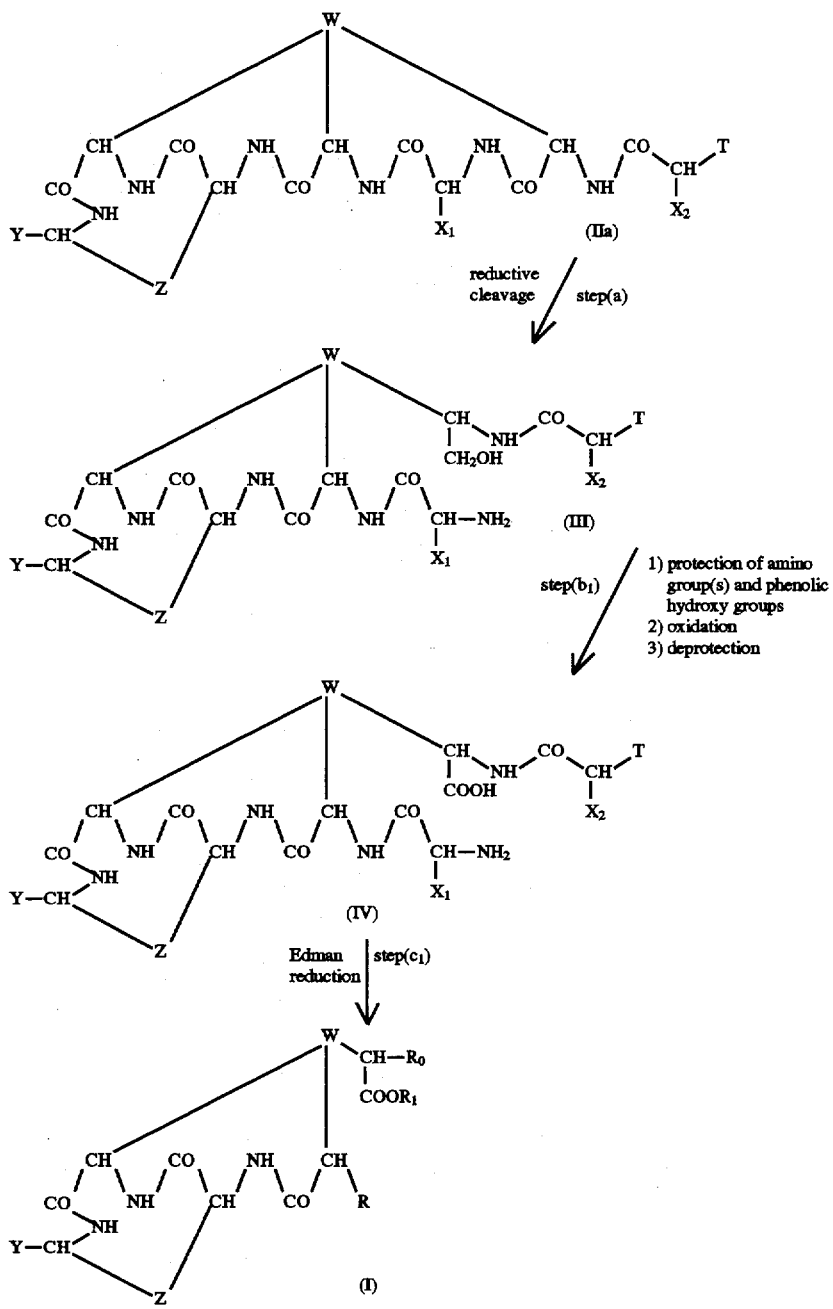

Reaction Scheme 2

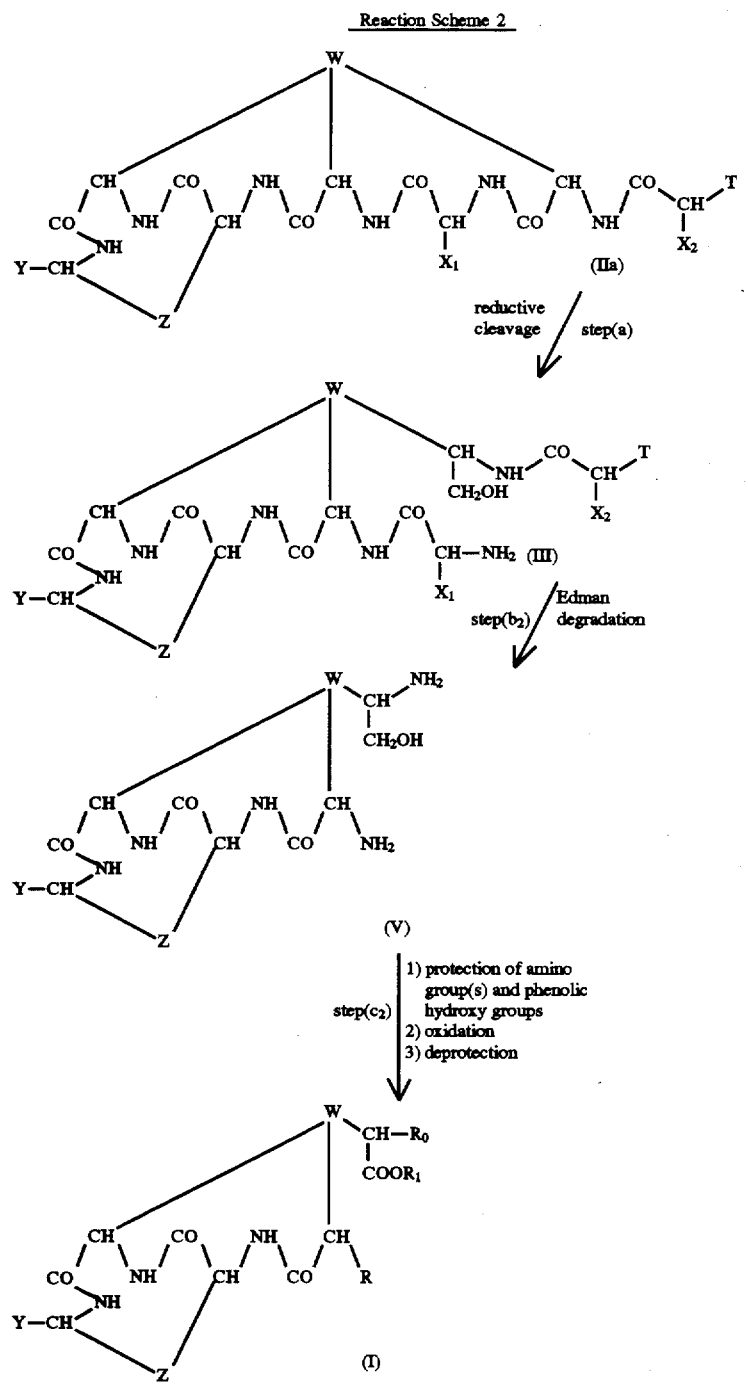

The first of which (step (a)), involves the reductive cleavage of the peptidic bond between the second and third amino acid (starting from the right) of the seven amino acids chain of the aglucodalbaheptide antibiotics of formula (IIa) to obtain a pentapeptide of formula (III) wherein W, Z, $X_1$ and $X_2$ represent the relative portions of the aglycon of an antibiotic of the dalbaheptide group, T represents amino, alkylamino or a protected amino group from which the original amino group can be readily restored, Y represents a carboxylic group or a functional derivative of said carboxylic group or the salts of the above represented pentapeptide antibiotics with acids or bases as well as their inner salts.

As explained above, this step (a) can also be carried out by using as the starting material the corresponding original glycosylated dalbaheptide or a pseudoaglycon thereof yielding a pentapeptide intermediate which still contains all or part of the typical sugar units. In said case, this intermediate is successively converted to the pentapeptide of formula (III) by removing the sugar moieties, for instance, by acid hydrolysis.

The method of preparation of these pentapeptides of formula (III) is already described in European Patent Application Publication No.409045 and, therefore, the novel process for the manufacture of the tetrapeptides of formula (I) as claimed in this application, actually starts with the successive steps (b₁), and (b₂) represented in Scheme 1 and Scheme 2, respectively.

These further reaction steps are following two different alternative pathways. One of these two alternative pathways involves first (step (b₁) of Rection Scheme 1) selectively protecting the free amino groups and all phenolic hydroxy groups of the above pentapeptide of formula (III) and then oxidizing the hydroxymethyl moiety to carboxy to obtain the corresponding carboxy derivative, which is subsequently deprotected at the amino group and, optionally, at the phenolic hydroxy groups, to yield a novel pentapeptide intermediate of the following general formula (IV) wherein W, Z, X₁ and X₂ represent the relative portions of the aglycon of an antibiotic of the dalbaheptide group, T is amino, alkylamino or a protected amino group from which the original amino group can be readily restored, Y represents a carboxylic group or a functional derivative of said carboxylic group, including the salts of the above represented pentapeptide with acids or bases as well as their inner salts.

The above pentapeptide intermediate (IV) is then submitted to a double Edman degradation (step (C₁)) that affords the product of formula (I) by elimination of the two amino acid moieties bearing the symbols X₁ and X₂ in the pentapeptide of formula (IV).

According to a variation of this reaction pathway which is comprised by Reaction Scheme 1, the above pentapeptide of formula (III) can be protected at the amino groups with a protecting group different from that utilized to protect the phenolic hydroxy groups and removable under conditions which do not alter the protection at said phenolic hydroxy group, so that, after oxidation of the hydromethyl group, the amino groups can be selectively deprotected.

The resulting oxidized pentapeptide, protected at the phenolic hydroxy groups, but possessing the unprotected amino groups, is then submitted to the double Edman degradation to yield final compound (I) still possessing the phenolic hydroxy group protected with the original protecting group which can be optionally removed at the end of the sequence of this reaction step.

The other reaction pathway leading to the tetrapeptide of formula (I) from the pentapeptide of formula (III) involves (step (b₂) of Rection Scheme 2) submitting first the pentapeptide of formula (III) to a double Edman degradation to eliminate the two amino acids bearing the symbol X₁ and X₂ to yield an intermediate of formula (V) wherein W, Z and Y have the same meaning as in formula (III) and including its salts with acids or bases as well as its inner salts. Then (step (c₂)), the primary amino groups and the phenolic hydroxy groups of said intermediate of formula (V) are selectively protected and the resulting compound is submitted to oxidizing conditions to convert the hydroxymethyl moiety to carboxy, yielding a compound of formula (I) wherein the amino groups and the phenolic hydroxy groups are protected. If desired, these groups can be deprotected by common procedures known in the art.

As it will be further explained in more detail, the symbol Y in the final tetrapeptides (I) may represent a carboxylic group or a functional derivative thereof which includes those derivatives containing a protecting group of the carboxylic function which can be introduced during one of the steps described above and which can be optionally removed either simultaneously with the removal of the other protecting groups or separately, under specific conditions.

As it is obvious to any person skilled in the art, if the starting material or the intermediate derivatives (II), (IV) and (V) contain further groups which can adversely affect the successive reaction step(s), they may be protected by introduction of suitable protective groups which can optionally be removed after the completion of the successive step(s).

If desired, a tetrapeptide of formula (I) wherein R₁ represents hydrogen may be transformed into the corresponding derivative wherein R₁ is a protecting group of the carboxylic function. Analogously, when a compound of formula (I) is obtained wherein R and R₀ each independently represents a free amino group, said compound can be optionally transformed into the corresponding derivative of formula (I) wherein R and R₀ each independently represents a protected amino group.

As described above, the dalbaheptide starting materials for the obtainment of the tetrapeptides of this invention are known compounds or may be prepared (aglucodalbaheptides) from the corresponding dalbaheptides by hydrolysis methods per se known in the art.

References 1–29 here below give some examples of aglucodalbaheptides and their obtainment. (See also the above mentioned paper by F. Parenti and B. Cavalleri at page 64).

According to a more specific description of most of the aglucodalbaheptide precursors so far known (or which can be prepared from the dalbaheptides so far known), the structure of which has been determined (which is not limiting the scope of this invention), the symbols W and Z in the aglucopeptide precursors of formula (IIa), in the intermediates of formulas (III), (IV) and (V) and tetrapeptide end compounds of formula (I) deriving therefrom, can respectively represent the following partial structures:

W =

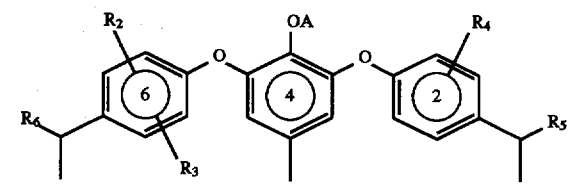

Z =

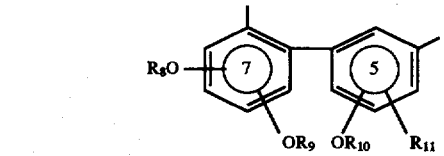

wherein:

i): A is hydrogen or a protecting group of the phenolic hydroxy rest; R₂, R₃ and R₄, are each independently, hydrogen or halogen wherein the halogen preferably is chloro or bromo and are most preferably in the ortho position with respect to the ether bond; R₅ and R₆ are each independently hydrogen, or a group OR₇ wherein R₇ is hydrogen or a protecting group of the benzylic hydroxy rest.

As shown in formula (IIa) above, the group W is simultaneously linked to the second, fourth and sixth amino acid (starting from the right) rest of the heptapeptidic chain of dalbaheptides;

ii): the groups OR₈ and OR₉, preferably, are respectively in the para and ortho position with respect to the bond connecting the two phenyl rings and the radical R₈ and R₉ each independently represents hydrogen or a protecting group of the phenolic hydroxy rest; the group OR₁₀ is, preferably, in the position ortho with respect to the bond connecting the two phenyl rings and the radical R₁₀ represents hydrogen or a protecting group of the phenolic hydroxy rest; the group R₁₁ is, preferably, in the position meta with respect to the bond connecting the two phenyl rings and represent hydrogen or halogen, most preferably, hydrogen or chloro.

As shown in formulas I, (IIa), III, IV and V above, the group Z is linked to the amino acids corresponding to the fifth and seventh amino acid (starting from the right) rests of the heptapeptidic chain of dalbaheptides.

The encircled numbers in the aromatic rings indicate the respective amino acids of the original dalbaheptide chain to which the specific aryl or aralkyl moiety is bound.

The meanings of the symbols $X_1$ and $X_2$ in formula (IIa) which permit the differentiation of the aglucodalbaheptides so far known (or that can be obtained from the dalbaheptides so far known) into four sub-groups are respectively the following:

$X_1$ represents a phenyl or a benzyl group wherein the phenyl ring may optionally bear one or two substituents selected from halogen, preferably chloro, lower alkyl, preferably methyl, and hydroxy, or it may also represent a $(C_1-C_2)$ aliphatic rest substituted with a carboxylic or carboxamide function, a thiomethyl or a methylsulfinyl group.

$X_2$ represents a phenyl group which may optionally bear one or two substituents selected from halogen, preferably chloro, lower alkyl, preferably methyl, and hydroxy or it may represent a $(C_1-C_4)$ aliphatic rest, preferably methyl or isobutyl.

$X_1$ and $X_2$ taken together may also represent a oxybis (phenylene) rest where one or both phenyl rings may optionally be substituted as indicated above.

The above meanings of the symbols $X_1$ and $X_2$ apply also to the intermediate derivatives of formula (III) and (IV) conditions which do not affect the amino acid chain. This definition includes the naturally occurring lower alkyl esters as well as the esters formed by reaction of the carboxylic function with alcohols, e.g. aliphatic alcohols optionally bearing substituents (e.g. hydroxy, halo, lower alkoxy, amino, lower alkylamino, di-(lower alkyl)amino, cyano and phenyl, optionally substituted by lower alkyl, lower alkoxy, halo or nitro) in the aliphatic chain, and includes also a wide series of substituted amides which are formed by reaction of the carboxy group with aliphatic, cycloaliphatic and heterocyclic amines. In particular, among the aliphatic amines, the lower alkylamines and the di-lower alkylamines are preferred and may optionally contain a substituent on the aliphatic chain such as amino, lower alkylamino, di-(lower alkyl)amino, pyrrolidino, piperazino, N-(lower alkyl) piperazino, morpholino, hydroxy, lower alkoxy, carboxy, carbo(lower alkoxy), carbamyl, mono- and di-(lower alkyl) carbamyl and the like; among the cycloaliphatic amines, the $C_4-C_7$ cycloaliphatic primary amines are preferred; among the heterocyclic amines saturated nitrogen containing 5 to 7 membered heterocyclic ring are preferred, e.g. pyrrolidine, morpholine, piperazine, and N-(lower alkyl)piperazine The above descriptions and definitions of the symbols W, Z and Y, when referred to the tetrapeptides derived from the above said aglucodalbaheptides, point to a preferred embodiment of this invention which is represented by the tetrapeptide derivatives of formula (Ia)

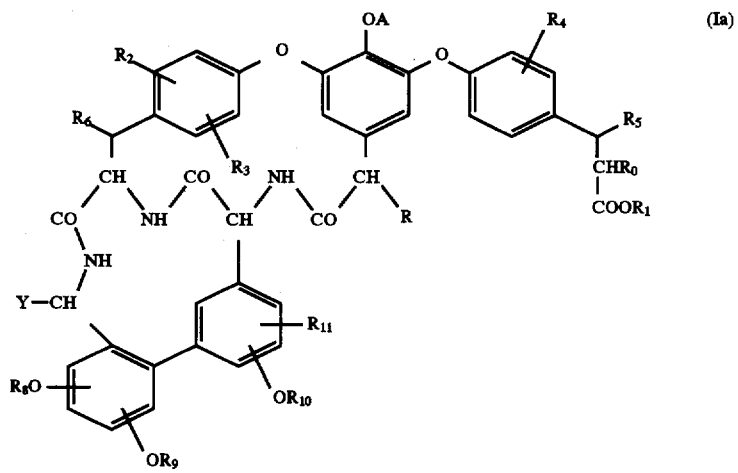

resulting from the respective precursor (IIa) according to the process of this invention.

For the purpose of a more specific representation of most of the aglucodalbaheptide precursors of formula (IIa) above so far known or which can be prepared from the corresponding dalbaheptides (including their semisynthetic derivatives) and of the intermediate derivatives of formulas (III) and (IV), the symbol T identifies an amino group wherein one hydrogen atom may optionally be substituted by an alkyl radical of 1 to 12 carbon atoms which, in turn, can optionally bear one or more substituents, by a $(C_4-C_7)$ cycloalkyl or T may represent a protected amino group whereby the original aminic group can be readily restored during one of the steps of the process preceding the Edman degradation (See Reaction Scheme 1 and 2)

The symbol Y in formulas (I), (IIa), (III), (IV) and (V) represents a carboxy group, a functional derivative thereof such as a carboxyester, a carboxamide or a carbohydrazide group and includes the protected carboxy groups from which the free carboxy group can be easily restored under specific wherein A, R, $R_0$, $R_1$, $R_2$, $R_3$, $R_4$, $R_5$, $R_6$, $R_7$, $R_8$, $R_{10}$, $R_{11}$ and Y have the same meanings as above The salts of the end compounds of formula (I), of starting compounds of formula (IIa) (or the corresponding glycosylated dalbaheptides of general formula (II)) and of the intermediates of formulas (III), (IV) and (V) can be those deriving from the salification with an acid of the basic functions of the molecule, e.g., the aminic functions resulting from the cleavage of the peptidic bond of the original dalbaheptide peptidic chain in the end compounds of formula (I) and in the intermediates of formulas (III), (IV) and (V), or the aminic function identified by the symbol T in both the starting materials of formula (IIa) and in the intermediates of formulas (III) and (IV), or an aminic function contained as substituent in the carboxyester, carboxamide or carbohydrazide moiety represented by the symbol Y in any of the compounds of formula (I), (IIa), (III), (IV) and (V). Representative acid addition salts are those formed by reaction with both inorganic and organic acids, for example, hydrochloric, sulfuric, phosphoric, succinic, citric, lactic, maleic, fumaric, cholic, d-glutamic, d-camphoric, glutaric, phthalic, tartaric, methanesulfonic, benzenesulfonic, benzoic, salicylic, trifluoroacetic acid and the like. Alternatively, the salts may be formed through salification of the carboxylic acid function represented by the symbol Y of the end compounds, intermediates or starting materials, or an acidic function contained as substituent in the carboxyester, carboxamide or carbohydrazide portion identified by the symbol Y or any acidic function which may be present in any other portion of the molecule, such as the carboxy group deriving from the cleavage of the original peptidic chain in the end compounds of formula (I) (COOR$_1$, R$_1$=hydrogen) and the intermediates of formula (IV), with an appropriate base, such as, for instance, an alkali metal hydroxide or carbonate or an organic amine, such as a mono-, di- or tri-(lower alkyl)amine and the like. The inner salts are those formed through internal salification in the cases of simultaneous presence of basic (e.g. amino) and acid (e.g. carboxy) functions of sufficient strength in the starting materials, intermediates and tetrapeptide end compounds.

The characteristics which allow a further classification of the so far known dalbaheptides into four-sub-groups are in no way limiting the scope of this invention in that new natural products and derivatives thereof falling into the general classification of dalbaheptide antibiotics can be obtained and can be converted to tetrapeptides of formula (I) according to the process of this invention. However, for a more precise identification of representative starting compounds that can be used according to this invention for obtaining the corresponding tetrapeptides of formula (I), in the following is given a further detailed description of the four dalbaheptide sub-groups mentioned above and of the tetrapeptides deriving from their corresponding aglycons according to a preferred embodiment of this invention.

Referring to the formula (II) above, the sub-group identified as ristocetin-type dalbaheptides is characterized by the fact that the symbols X$_1$ and X$_2$ taken together represent an oxybis(phenylene) rest wherein one or both phenyl rings may optionally bear one or two substituent selected from halogen, preferably chloro, lower alkyl, preferably methyl, and hydroxy wherein the hydroxy group can be optionally conjugated with a sugar moiety through an acetalic bond or esterified with a sulfuric acid residue.

Other dalbaheptide antibiotics which can be assigned to this sub-group include the followings actaplanin, teicoplanin, antibiotic A 35512, antibiotic A 41030, antibiotic A 47934, ardacin A, B, C, antibiotic A 46926, kibdelin (ref. 24), parvodicin, and antibiotic UK 68597. (See pertinent references in European Patent Application Publication No. 469645).

The semisynthetic derivatives of the above mentioned natural products are also included in this sub-group. See, for instance, the aglycone and pseudoaglycones of ardacins and the derivatives thereof wherein Y is a carboxamide or a carbohydrazide rest; the aglycone and pseudoaglycone of parvodicin; the hydrolysis products of actaplanins; the acylation derivatives of ristocetin, actaplanin and their pseudoaglycons, the bromine analogs of actaplanin; the aromatic aldehyde derivatives of ristocetin; the derivatives of teicoplanin and antibiotic A 46926 which are more specifically considered below. (See pertinent references in European Patent Application Publication No. 409045).

Accordingly, one of the objects of this invention consists in the tetrapeptides deriving from the ristocetin-type aglucodalbaheptides which can be formally represented through formula (IIa) above where W, Z, T and Y are defined as above, X$_1$ and X$_2$ are as specifically defined for the identification of the ristocetin-type dalbaheptides sub-group with the proviso that any sugar unit is removed.

For example, from aglucoristocetin (Y=COOCH$_3$) and its corresponding acid (Y=COOH) which have the following formula (IIb):

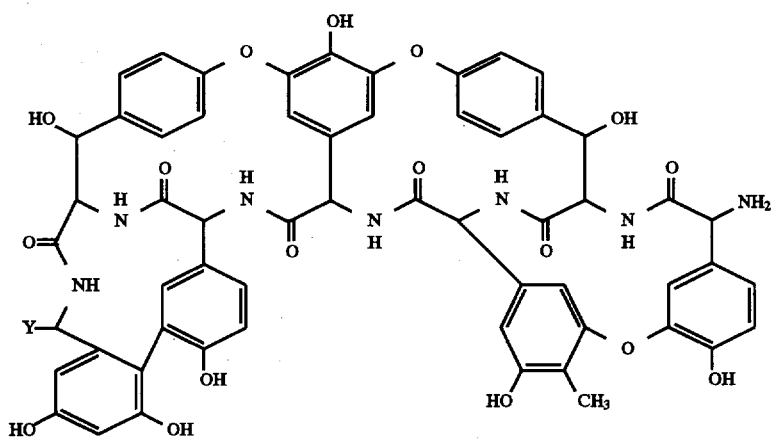

(IIb)

the corresponding specific tetrapeptide of formula (Ib) can be derived according to this invention

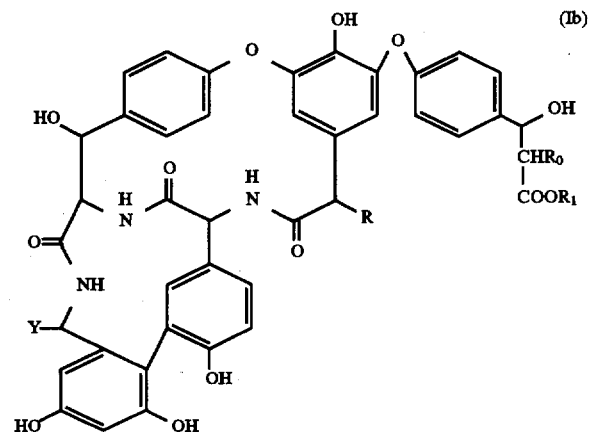

(Ib)

wherein:

R, R$_0$, and R$_1$ have the same meaning as above;

Y represents a carboxylic group, carbomethoxy or another protected carboxylic group;

and the phenolic hydroxy groups may optionally be protected.

The starting aglucoristocetin and its correspoding acid may be obtained according to the literature from ristocetin A or B and their pseudoaglycones (See references 1, 2, 3 and 4).

Aglucoteicoplanin and its semisynthetic derivatives of formula (IIc)

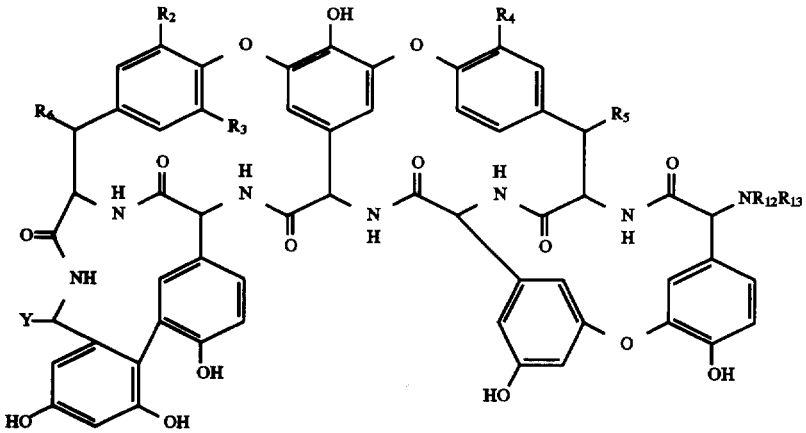

(IIc)

represents a particular group of precursors which can be assigned to the ristocetin-type aglucodalbaheptides and which can be transformed into the corresponding tetrapeptides of formula (Ic) according to this invention

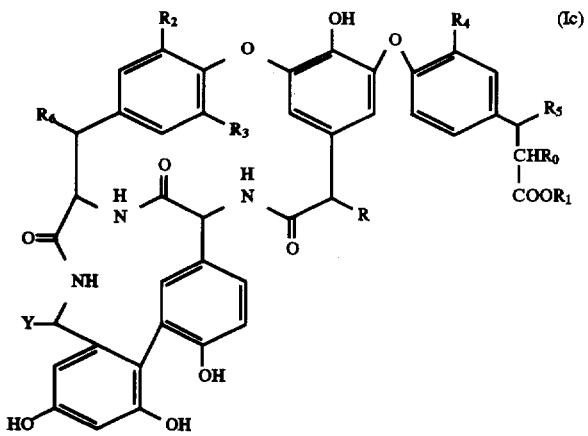

(Ic)

In the above formula (IIc), when representing aglucoteicoplanin, $R_2$, $R_5$, $R_{12}$ and $R_{13}$ are hydrogen, $R_3$ and $R_4$ are chloro, $R_6$ is hydroxy and Y is a carboxylic group (Ref. 5, 6).

The corresponding tetrapeptide derived from aglucoteicoplanin according to this invention is represented by formula (Ic) wherein R, $R_1$ and $R_0$ have the same meaning as above, $R_2$ and $R_5$ are hydrogen, $R_3$ and $R_4$ are chloro, $R_6$ is hydroxy, and Y is a carboxylic group or a protected carboxylic group and the phenolic hydroxy groups may optionally be protected.

A series of derivatives of teicoplanin and aglucoteicoplanin is known or may be prepared (aglucoteicoplanin derivatives) from the corresponding teicoplanin semisynthetic derivatives wherein (formula (IIc)) at least one of the symbols Y, $R_3$, $R_4$, $R_6$, $R_{12}$ and $R_{13}$ assumes a meaning different from those listed above for the identification of aglucoteicoplanin. For instance: the symbol Y of the formula (IIc) above may represent a functional derivative of the carboxylic group such as a carboxyester, e.g. a lower alkyl ester wherein the alkyl moiety may optionally contain a further substituent such as, for example, hydroxy, lower alkoxy, amino, lower alkylamino, di-(lower alkyl)amino, cyano, halo and phenyl, optionally substituted by lower alkyl, lower alkoxy, halo or nitro (Int. Appln. Publ. No. WO./8600075), a carboxamide, or, preferably, a substituted carboxamide, for example, an amide with a lower alkyl amine wherein the lower alkyl moiety may optionally contain a substituent selected from amino, lower alkylamino, di-(lower alkyl)amino, pyrrolidino, piperazino, N-(lower alkyl)piperazino, morpholino, hydroxy, lower alkoxy, carboxy, carbo(lower alkoxy), carbamyl, mono- and di-(lower alkyl)carbamyl or an amide with a di-(lower alkyl) amine, or an amide with a saturated 5 to 7 membered heterocylic ring, e.g., pyrrolidine, morpholine, piperazine and N-(lower alkyl)piperazine, (E.P.A. Publ. No. 218099, Int. Pat. Appln. Publ. No. WO/06600, Int. Pat. Appln. Publ. No. WO 90/11300 and E.P.A. Publ. No. 370283); the rest $NR_{12}R_{13}$ can represent an amino group modified by reaction with a readily removable protecting group or by conversion into alkylamino e.g. lower alkylamino wherein the alkyl portion may bear further substituents such as those disclosed above (see E.P.A. Publ. Nos. 276740, 351597 and 351685); each of the groups $R_3$, $R_4$ and $R_6$, independently, may represent hydrogen (ref. 7, 8, 9).

Each of the above mentioned modifications in the different portions of the aglucoteicoplanin molecule may occur independently (i.e. only one variation does occur while all other meanings of the symbols defining aglucoteicoplanin remain unchanged) or simultaneously (see e.g. E.P.A. Publ. Nos. 352538 and 370283), yielding suitable precursors for the obtainment of tetrapeptide derivatives of this invention of formula (Ic) wherein the symbols $R_2$, $R_3$, $R_4$, $R_5$, $R_6$ and Y have the same meanings as those of the corresponding starting materials, R, $R_0$ and $R_1$ have the same meanings as above and the phenolic hydroxy groups may optionally be protected. Of course, if the modified portion(s) of the starting teicoplanin derivatives contain substituent(s) which may be affected by the reaction conditions of one or more step of the process of this invention, they may be conveniently protected before undergoing the specific reaction(s) course and then, optionally, deprotected at the end of the process.

A further particular group of compounds falling within the ristocetin-type aglucodalbaheptides sub-group comprises the aglycon of antibiotic A 40926 complex (ref. 12). Also this compound or its corresponding glycosylated dalbaheptides are suitable starting materials for conversion into the corresponding tetrapeptides embraced by the general formula (I) through the process of this invention.

The dalbaheptide antibiotic sub-group identified as vancomycin-type dalbaheptides is characterized by the fact that (reference is made to formula II above) the symbol $X_1$ represents a $(C_1-C_2)$aliphatic rest substituted with a carboxylic group or carboxamide function and the symbol $X_2$ represents a $(C_1-C_4)$aliphatic rest. In particular, in the most common examples of antibiotic substances falling within this sub-group, $X_1$ is a residue deriving from aspartic acid, aspargine or glutamine, while $X_2$ is a residue deriving from alanine or leucine.

Other dalbaheptide antibiotics which can be assigned to this sub-group include the following: A 51568 A and B, orienticins, eremomycin, A 42867, A 82846, chloroorienticins, MM 47761 and MM 49721, decaplanin, MM 45289 and MM 47756. All these dalbaheptide antibiotics are well known to those skilled in the field. (See also pertinent references in European Patent Application Publication No. 409045).

The semisynthetic derivatives of the above mentioned natural products are included in this sub-group. See for instance: the various glycosylated derivatives of the hydrolysis products of vancomycin, A 51568A and B; the desvancosaminyl and des(vancosaminyl-O-glucosyl)- derivatives of vancomycin, A 51568A; A 51568B, and the derivatives of A 82846; the reaction products of the aminic rests of some vancomycin-type dalbaheptides with aldehydes and ketones and the corresponding hydrogenation products, the N-acyl derivatives of vancomycin-type antibiotics, mono- and didechlorovancomycin and the hydrolysis products of eremomycin. All these dalbaheptide antibiotics are well known to those skilled in the field. (See also pertinent references in European Patent Application Publication No. 409045).

Accordingly, one of the objects of this invention consists in the tetrapeptide deriving from the vancomycin-type aglucodalbaheptides which can be formally represented through the formula (IIa) above where W, Z, T and Y are defined as above, $X_1$ and $X_2$ are as specifically defined for the identification of the vancomycin-type dalbaheptide sub-group, with the proviso that any sugar unit is removed.

For example, aglucovancomycin (ref. 10, 11) has the following structure formula (IId):

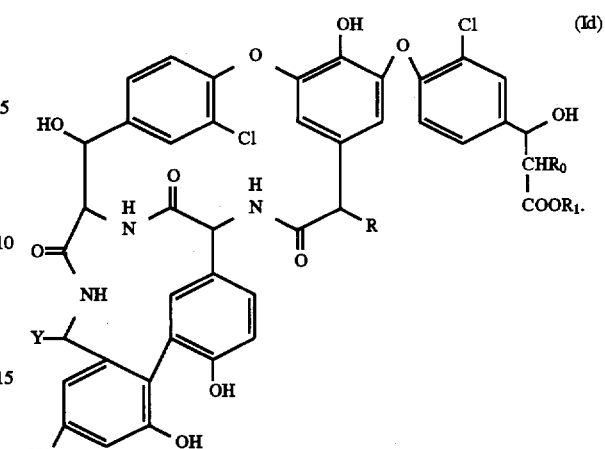

wherein:

R, $R_0$ and $R_1$ have the same meaning as above;

Y is a carboxylic or a protected carboxylic group; and the phenolic hydroxy groups may optionally be protected.

The avoparcin-type dalbaheptide sub-group is characterized by the fact that:

the symbol $X_1$ in the general formula (II) represents a phenyl or benzyl group wherein the phenyl ring may optionally bear one or two substituents selected from hydroxy and halogen, preferably chloro; the symbol $X_2$ represents a phenyl group which may optionally bear one or two substituents selected from halogen, preferably chloro, and hydroxy which may optionally be conjugated with a sugar moiety (e.g. rhamnose).

Other dalbaheptide antibiotics which can be assigned to this group include the following: actinoidin A, B, chloropolysporin A, B, C, actinoidin $A_2$ and helvecardin A, B, MM 47767, MM 55256. Semisynthetic derivatives of avoparcin-type sub-group of dalbaheptide antibiotics are for instance the demannosyl chloropolysporin B derivatives, the chloropolysporin pseudoaglycone, the derhamnosyl α- and β-avoparcin, the mannosyl aglycones of avoparcin (LL-AV290) and other derivatives wherein one or more sugar moieties are hydrolyzed. All these dalbaheptide antibiotics are well known to those skilled in the field. (See also

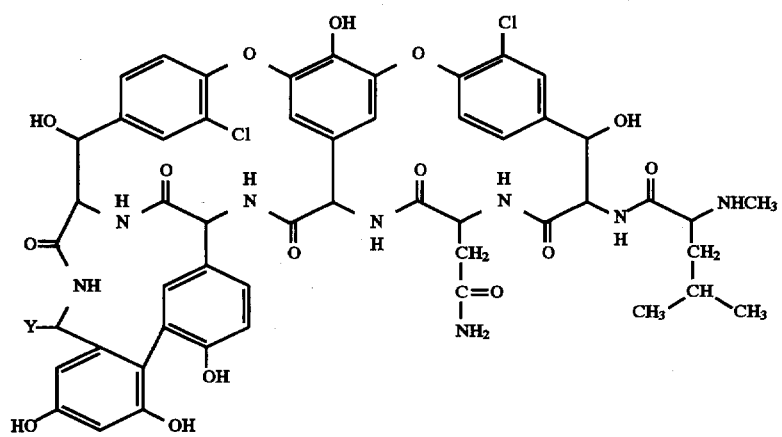

wherein Y is a carboxylic group.

According to this invention, the corresponding tetrapeptide of formula (Id) can be derived from aglucovancomycin:

pertinent references in European Patent Application Publication No. 409045).

Accordingly, one of the objects of this invention consists in the tetrapeptides deriving from the avoparcin-type aglucodalbaheptides which can be generally represented through formula (IIa) above where W, Z, T and Y are defined as above, $X_1$ and $X_2$ are as specifically defined for the identification of the avoparcin-type dalbaheptide sub-group with the proviso that any sugar unit is removed.

For example, (α- and β-aglucoavoparcin (ref. 13, 14) have the following structure formula (IIe):

wherein:
R, $R_0$ and $R_1$ have the same meaning as above;
Y is a carboxylic or a protected carboxylic group;
and the phenolic hydroxy groups may optionally be protected.

The dalbaheptide antibiotics sub-group identified as synmonicin-type antibiotics is characterized by the fact that

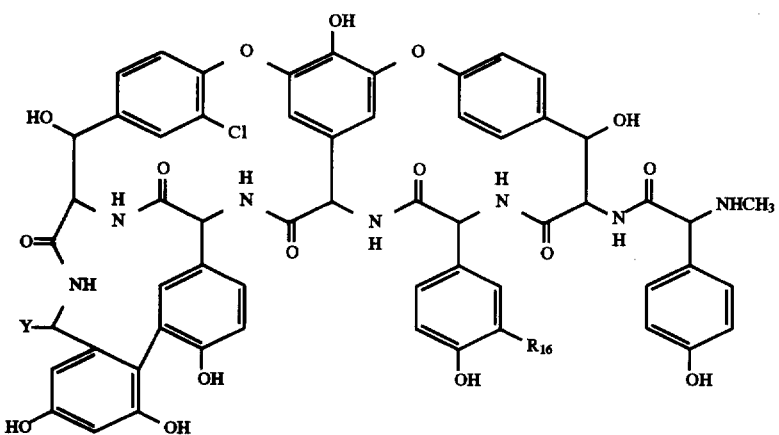

(IIe)

wherein:
Y is a carboxylic group;
and $R_{16}$ is hydrogen or chloro.

According to this invention, from α- and β-aglucoavoparcin a tetrapeptide of formula (Ie) can be derived

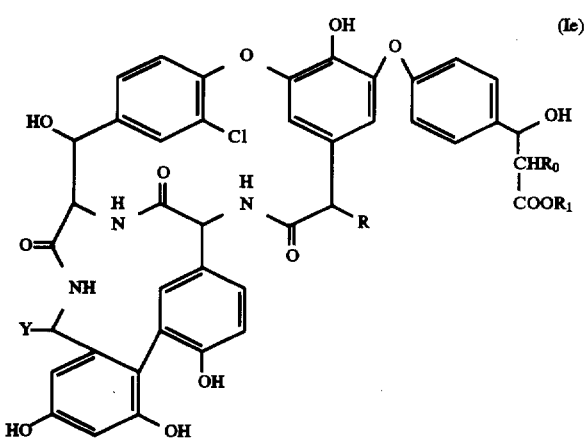

(Ie)

(reference is made to formula II above): the symbol $X_1$ represents a $C_2$ alkyl rest substituted on the terminal carbon with a thiomethyl or methylsulfinyl group; and the symbol $X_2$ represent a phenyl group bearing a hydroxy substituent which may be conjugated with a sugar moiety. Synmonicin (CWI-785) complex, its components and some of its hydrolysis products seem to be, for the moment, the only members of this sub-group. (See pertinent references in European Patent Application Publication No. 409045).

Accordingly, one of the objects of this invention consists in the tetrapeptides deriving from the synmonicin-type aglucodalbaheptides which can be formally represented through formula (IIe) above where: W, Z, T and Y are defined as above; $X_1$ and $X_2$ are as specifically defined for the identification of the synmonicin-type dalbaheptide sub-group with the proviso that any sugar unit is removed.

For instance, aglucosynmonicin A and B (ref. 15, 16) have the following structure formula (IIf):

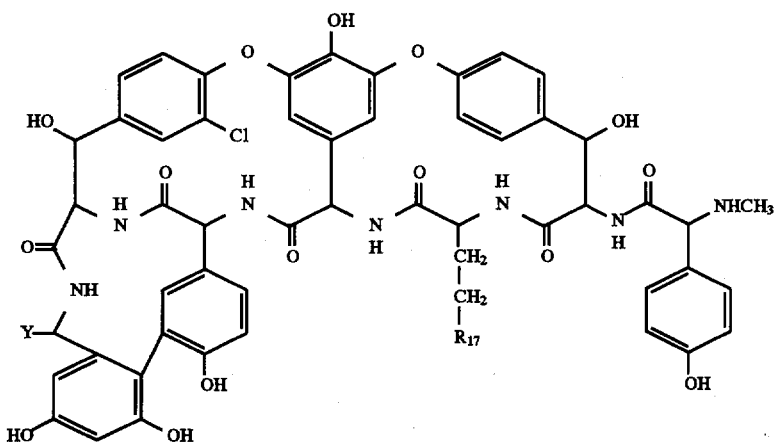

(IIf)

wherein:

Y is a carboxylic group;

and $R_{17}$ is methylsulfinyl or thiomethyl.

According to this invention a tetrapeptide derivative of the same formula (Ie) above can be derived from both aglucosynmonicin A and B.

The tetrapepetides of formula (I) are useful as intermediates for the preparation of synthetic aglucodalbaheptides wherein the first and third amino acids constituents, that is, those which in formula (IIa) bear the substituents $X_2$ and $X_1$, can be introduced by the skilled chemist through the insertion of the appropriate amino acid units into the tetrapeptide moiety by means of peptide chemistry reactions.

In the following description are given more specific details on the way the specific steps of the process may be carried out.

Step (a):

The procedure of the first step of the process for preparing the tetrapeptides of this invention from aglucodalbaheptides is extensively described in European Patent Application Publication No. 489045 and comprises submitting a aglucodalbaheptide antibiotic as defined above in a hydroalcoholic medium to a reductive cleavage with an alkali metal borohydride, preferably selected from sodium borohydride, potassium borohydride and sodium cyanoborohydride at a temperature comprised between 0° C. and 40° C.

The hydroalcoholic medium is a mixture of $H_2O$ and a lower alkanol wherein the ratio $H_2O$/alcohol ranges between 40/60 and 90/10 (v/v), preferably between 60/40 (v/v) and 70/30 v/v, most preferably is 65/35 (v/v). Although the reaction occurs, in some cases, also in the presence of lower amounts of water, e.g. in mixtures $H_2O$ alcohol 30/70 or 28/80, in general, the reaction rate is very low when the ratio $H_2O$/alcohol is lower than 40/60.

Preferred lower alkyl alcohols are linear and branched ($C_1$–$C_4$) alkyl alcohols, among which the most preferred is ethanol.

In a particular preferred embodiment of this step of the process a hydroalcoholic mixture $H_2O$ ethanol 65/35 (v/v) is used.

Sometimes, in particular cases, a small amount of a polar co-solvent can be added to completely dissolve the dalbaheptide starting material during the course of the reaction, e.g. N,N-dimethylformamide, 1,3-dimethyl-3,4,5,6-tetrahydro-2(1H)-pyrimidone (DMPU), dimethylsulfoxide. In some cases, a small amount of n-butanol can be added to minimize foaming.

As alkali metal borohydride the sodium borohydride is the most preferred one. The suitable amount of alkali metal borohydride employed may vary depending on the particular compound used as starting material, the solvent used and the temperature of the reaction, but it is advisable to use an amount of alkali metal borohydride in a large excess over the stoichiometric requirement in such a way that the pH of the reaction mixture is alkaline, preferably between pH 8 and 12. Anyway, in general, the molar ratio between the alkali metal borohydride and the antibiotic starting material is comprised between 50 and 300.

The reaction temperature may vary considerably depending on the specific starting materials and reaction conditions. In general, it is preferred to conduct the reaction at a temperature between 0° and 40° C., more preferably at room temperature. Also the reaction time may vary considerably depending on the other reaction parameters. In general, the reaction is completed in about 10–48 hours. In any case, the reaction course is monitored by TLC or, preferably, by HPLC according to methods known in the art. On the basis of the results of these assays a man skilled in the art will be able to evaluate the reaction course and decide when to stop the reaction and start working up the reaction mass according to known per se techniques which include, for instance, extraction with solvents, precipitation by addition of non-solvents, etc., in conjunction with further separations and purification by column chromatography, when needed.

After the reaction is completed, in most cases, but not necessarily in all cases, mostly depending on the starting dalbaheptide, a clear solution is formed; then the excess of the alkali metal borohydride is eliminated by adding a suitable amount of an acid, for example, a ($C_1$–$C_4$)alkyl organic acid, a ($C_1$–$C_6$)alkyl sulfonic acid, an aryl sulfonic acid and the like, dissolved in a polar protic solvent such as, for example, a ($C_1$–$C_4$)alkyl alcohol.

According to Europan Patent Application Publication No. 409045, the pentapeptides of formula (III) may be alternatively prepared by hydrolysis of the corresponding glycosylated pentapeptides which, in turn, are obtained by applying the reductive cleavage process to the glycosylated dalbaheptides of general formula (II). By following this route the glycosylated pentapeptide obtained from the reductive cleavage is transformed in the corresponding aglucopentapeptide of formula (III) by submitting it to selective hydrolysis conditions such as those described in E.P.A. Publ. No. 146053 or E.P.A. Publ. No. 376042. In some cases, this is a preferred procedure for the lower amount of reducing agent required, shorter reaction time and higher reaction yield. In addition, in particular in the case of teicoplanin, side-epimerization is minimized.

The pentapeptide compounds resulting from the reductive cleavage step described above can be directly isolated in the form of free bases or salts with acid or bases as described above or can be utilized as such for the further steps ($b_1$) or ($b_2$).

Step ($b_1$):

A crucial point of this step consists in the appropriate selection of the protecting groups. In fact, the selective protection of the primary amino group resulting from the reductive cleavage step, of the amino group of the terminal amino acid and of the phenolic hydroxy groups of the pentapeptide (III) is essential to avoid undesidered modifications of the substrate during the oxidation reaction to convert the hydroxymethyl group resulting from the reductive cleavage to carboxylic group. Therefore, the protecting groups selected must be resistant to the oxidation conditions and must be readily removable after the oxidation process without altering the basic structure of the molecule. If necessary, protective groups can also be introduced on other oxidation sensitive rests of the substrate (III), e.g. the benzylic hydroxy rests which can be identified by the symbols $R_5$ and $R_6$ or in other portions of the molecule which are sensitive to the oxidation conditions applied. However, in some cases, for instance with a substrate (III) deriving from aglucoteicoplanin and its derivatives, it has been observed that the benzylic hydroxy group represented by the symbol $R_6$ is inert to both the oxidation reaction and the protecting agents. Also in the case of a substrate (III) deriving from aglucovancomycin, both benzylic hydroxy groups represented by the symbols $R_5$ and $R_6$ are inert to both the oxidation reagents and the reagents used to introduce the protecting groups.

The protective groups of the amino moiety and of the phenolic hydroxy groups (and of any other oxidation sensitive groups, when needed) can be either of the same or different type, depending on the reagents and conditions applied in the oxidation reaction. The type of substrate (III) is also to be considered for selecting the appropriate way and type of protection. Protecting groups and the relative procedures for their introduction and removal are described, for instance, in: T. W. Greene, "Protective Groups in Organic Synthesis", J. Wiley, N.Y., 1981.

In general, acyl radicals may be usefully employed for the protection of both amino and phenolic hydroxy groups. Said acyl radicals may be removed by hydrolysis, solvolysis or reduction depending on their nature. Typical examples of these acyl radicals are lower alkanoyl radicals optionally substituted by halogen or lower alkoxy such as, acetyl, chloroacetyl, dichloroacetyl, trifluoroacetyl, methoxyacetyl, benzoyl radicals optionally substituted by nitro groups such as benzoyl, 2-nitrobenzoyl and 2,4-dinitrobenzoyl, lower alkoxycarbonyl radicals optionally substituted by halogen such as methoxycarbonyl, ethoxycarbonyl, tert-butoxycarbonyl, 2-bromoethoxycarbonyl, 2,2,2-trichloroethoxycarbonyl, 2,2,2-trifluoro-ethoxycarbonyl or 2,2-dimethyl-2,1,1-trichloro-ethoxycarbonyl, phenyl-lower alkoxycarbonyl radicals optionally substituted on the phenyl group such as benzyloxycarbonyl, 4-nitrobenzyloxycarbonyl and 4-methoxybenzyloxycarbonyl and 3,4-methoxybenzyloxycarbonyl.

Typical protective groups of the phenolic hydroxy rests are those forming an ether which is resistant to the oxidation process and can be removed under conditions which do not affect the remaining portions of the molecule. Examples of said ethers are ethers with lower alkyl radicals optionally substituted by halogen or lower alkoxy, such as methyl, ethyl, t-butyl, trichloroethyl, methoxymethyl and methoxyethyl, ethers with phenylmethyl radicals wherein the phenyl group may optionally be substituted by nitro or lower alkoxy such as benzyl, 2-nitrobenzyl and 4-methoxybenzyl, ethers with lower alkanoylmethyl or benzoylmethyl radicals optionally substituted on the lower alkanoyl and benzoyl portion such as acetylmethyl, dichloroacetylmethyl, trifluoroacetylmethyl, benzoylmethyl, 4-chloro- or 4-bromo-benzoylmethyl, 4-nitrobenzoylmethyl, ethers with fully hydrogenated heterocyclic radicals of 5 to 7 members containing one oxygen atom such as 2-tetrahydrofuranyl- and 2-tetrahydropyranylether.

For example, when it is desired to protect in a different way the amino groups and the phenolic hydroxy groups according to the process variation mentioned before, the amino groups can be protected with tert-butoxycarbonyl radicals, while the phenolic hydroxy group may be protected with benzyloxycarbonyl radicals.

For carrying out step ($b_1$), as well as other steps of the process of this invention, it is not necessary to protect the carboxylic group which may be identified by the symbol Y, but it may be desirable to obtain a tetrapeptide (I) wherein the carboxylic group represented by Y is protected by a group which can be useful or necessary in the successive use of tetrapeptide (I) as intermediate for the preparation of synthetic aglucodalbaheptides. Therefore, in said case, it may by suitable to have introduced the protecting group of said carboxylic function (when it is not already present in the original dalbaheptide or aglucodalbaheptide) in the earlier reaction steps of the process of this invention. For instance, the carboxylic function is suitably protected when transformed in esterified form, the ester group being readily cleavable under reductive or solvolytic conditions. Accordingly, most of the groups mentioned above for the protection of the phenolic hydroxy group can be utilized also for the protection of the carboxylic function. For instance, esterification with lower alkyl, phenylmethyl and benzoylmethyl radicals wherein the lower alkyl and the phenyl portion may optionally be substituted as described above, results in a suitable protection of the carboxylic function.

According to a preferred embodiment of the invention, the amino groups are protected in a first stage by introduction of a lower alkoxycarbonyl or a phenyl-lower alkoxycarbonyl radical, for instance, a tert-butoxycarbonyl or benzyloxycarbonyl radical. For this purpose, the pentapeptide of formula III is reacted with a reagent capable of inserting said radical onto the amino group such as di-tert-butylcarbonate, di-tert-butyl-dicarbonate, 2,4,5-trichlorophenyl-tert-butylcarbonate or benzyl chloroformate in the presence of an excess of a mild base. The reaction is usually carried out in the presence of a solvent at a temperature between 0° and 50° C., preferably between 15° and 25° C. Usually, the reagent providing the protecting group is employed in about equimolecular amount or in a slight excess with respect to number of the amino groups of the pentapeptide (III) which require protection during the oxidation step. In the usual cases, where the amino groups of the pentapeptide requiring protection are two (the one of the first amino acid and the one resulting from the reductive cleavage of the previous step (a)), about two equimolecular amounts of protecting agent for each equimolecular amount of pentapeptide are employed. The solvent is preferably selected from the mixtures of water and a water miscible organic solvent, when di-(lower alkyl)carbonates or di-(lower alkyl)dicarbonates are used as reagents providing the protecting groups. The water miscible organic solvent is usually selected from lower alkanols, acetone, tetrahydrofuran and dioxane. The proportion between water and water miscible solvent is varying between 1:9 and 9:1, preferably between 4:6 and 6:4.

With reagents like the 2,4,5-trichlorophenyl-tert-butylcarbonate and benzyl chloroformate, polar organic solvents like dimethylformamide or dimethylsulfoxide and their mixture with a lower alkanol, acetone, tetrahydrofuran and dioxane are preferred.

The mild bases which are preferably utilized are selected from alkali metal carbonates, alkali metal bicarbonates (e.g. potassium carbonate and sodium bicarbonate), tri-(lower alkyl)amines (e.g. triethylamine), and mixtures thereof.

According to the above mentioned preferred procedure, the protection of the phenolic hydroxy groups is effected in a second stage through the formation of ethers, esters, or carbonate esters as described above such as, for instance, lower alkyl ethers, benzyl ethers and benzoylmethyl ethers wherein the alkyl and phenyl moiety may optionally be substituted as indicated above, or lower alkanoyl esters, benzoyl esters, lower alkoxycarbonyl esters and benzyloxycarbonyl esters wherein the alkyl and phenyl moiety may optionally be substituted as indicated above.

The formation of the above mentioned ethers may be carried out, for instance, by reaction of the pentapeptide (III) protected on the amino groups with a reagent consisting of the appropriate ether forming a radical bound to a suitable living group, such as a lower alkyl, benzyl or benzoylmethyl chloride, bromide, sulfate, or p-toluenesulfonate in the presence of an excess of a base and a polar organic solvent, for instance, dimethylformamide or dimethylsulfoxide, preferably under anhydrous conditions. Suitable bases are selected from alkali metal carbonates, e.g. sodium carbonate, potassium carbonate, and cesium carbonate and tri-(lower alkyl) amines, e.g. triethylamine, tributylamine and methyldibutylamine. The temperature of the reaction ranges from $-10°$ to $40°$ C., preferably from $10°$ to $25°$ C.

The formation of the esters may be carried out, for instance, by reaction of the same pentapeptide (III) protected on the amino groups with a suitable acylating agent consisting of the appropriate protective acyl group bound to a leaving group such as a lower alkanoyl, benzoyl, lower alkoxycarbonyl, benzyloxycarbonyl chloride or bromide or a corresponding reactive ester or anhydride. The reaction is usually carried out in the presence of an organic solvent, and an excess of a base, preferably under anydrous conditions. The solvent is preferably selected from the polar organic solvents, e.g. dimethylformamide or dimethylsulfoxide, and their mixtures with acetone, tetrahydrofuran, and dioxane.

In some cases, for instance, when a benzyloxycarbonyl protecting group is used for the phenolic hydroxy groups, a mixture of the above organic solvents with water, preferably in a 1:1 proportion is a suitable solvent mixture. In fact, under these conditions, the reactivity of the primary hydroxymethyl group toward the protecting agents is minimized. The base is usually selected from alkali metal carbonates, e.g. sodium carbonate, potassium carbonate and cesium carbonate (as all preferred ones), and the organic tertiary bases, e.g. the tri-(lower alkyl) amines such as triethylamine, tributylamine and the like. The temperature of the acylation reaction usually ranges between $5°$ and $35°$ C., preferably $15°$ and $20°$ C.

In both ethers and esters formation, the reagent is usually added portionwise during a certain interval of time to reach a final amount which is in a 2 to 6 molar excess over the stoichiometric amount necessary to protect all the hydroxy groups (apart from the hydroxy group of the hydroxymethyl rest) of the pentapeptide substrate which are not inert to the successive oxidation.

In most cases described above the introduction of ether protecting groups affords also the formation of the corresponding ester of the original carboxylic moiety identified by the symbols Y in the pentapeptide (III), when it is not already transformed into a functional derivative thereof.

Although the main target of these protective steps is to selectively protect all amino and the hydroxy groups which are sensitive to the successive oxidation, with the exception of the hydroxymethyl rest produced by the previous reductive cleavage, the resulting protected pentapeptide derivative may not be a unitary product, but, rather, it may contain a certain amount of product(s) which present(s) a lower degree of protection or, even, may contain a certain amount (s) of product(s) protected at undesired position(s) such as the hydroxymethyl moiety. However, it may not be practical to eliminate these products from the mixture resulting from this second step ($b_1$) of the process of the invention, but, it may be more practical to use this crude product, without submitting it to any special purification procedure, in the successive oxidation reaction.

The selection of the oxidizing agent and the relative reaction pH essentially depend on the protecting groups utilized in the previous stages. Although several oxidation reagents and pH conditions have been tested, satisfactory results have been achieved only by using potassium permanganate at a neutral or basic pH or, preferably, the so called Jones reagent, i.e. chromium trioxide in diluted sulfuric acid.

With potassium permanganate as the oxidizing agent the reaction is conducted at pH between 7 and 12, preferably, between 8.5 and 12, in aqueous conditions, preferably in the presence of a water miscible organic solvent such as acetone, tetrahydrofuran or dioxane. With Jones reagent, the reaction is carried out by adding portionwise an excess of a standard solution of Jones reagent to a solution of protected pentapeptide in an organic solvent miscible with water such as acetone, tetrahydrofuran or dioxane at a temperature between $15°$ and $35°$ C., preferably between $20°$ and $30°$ C. The reaction product from the oxidation reaction is isolated according to the usual procedures known in the art which imply elimination of the reduced inorganic materials and the reagent excess which, in general, is decomposed before elimination, and may be submitted to the successive deprotection stage without any particular purification.

The procedures followed for the removal of the protecting groups from the oxidation product depend on the type of the protecting groups utilized.

As mentioned above, acid or base catalyzed solvolysis, hydrogenolysis or reductive cleavage are the usual methods applied for the removal of the protective groups. The more appropriate methods may be selected by the skilled technician also by relying on the indications given in the text book indicated above. For instance, when the amino or hydroxy groups are protected by way of esters with the benzyloxycarbonyl groups or ethers with the benzyl radical, catalytic hydrogenation may represent the most preferred deprotection procedure. The hydrogenation is usually carried out at room temperature at a pressure which corresponds to the atmospheric pressure or of 1–2 atmospheres over the atmospheric pressure, in the presence of an hydrogenation catalyst, e.g. 5% to 10% $Pd/BaSO_4$ or 5% Pd/C, an inert organic solvent such as lower alkanols, dimethylformamide, dioxane, tetrahydrofuran and their mixtures, and an acid, for example, glacial acetic acid or a diluted aqueous mineral acid, e.g. 0.1N hydrochloric acid. The removal of the acyl groups such as lower alkanoyl or (lower alkoxy)carbonyl from the amino or hydroxy groups may be carried out by acidolysis, or acid or basic hydrolysis, for example with diluted alkyl hydroxides or diluted mineral acids, or with strong organic acids. For instance, the tert-butoxycarbonyl groups protective of the aminic functions can be suitably removed from the oxidized product by dissolving the oxidized product in trifluoroacetic acid at room temperature and stirring the solution for 1-3 hours and then evaporating the obtained solution under reduced pressure. The deprotected product (IV) may be isolated according to procedures per se known in the art and, if needed, purified by means of reverse-phase column chromatography, for instance, by loading a solution of the above mentioned deprotected product (IV) in aqueous acetonitrile at a pH between 3 and 4 on a silanized silica-gel column and then developing the column with a linear gradient of acetonitrile in water (e.g. 15% v/v to 50% v/v) and collecting the eluted fractions under HPLC control.

Step ($c_1$):

The Edman degradation and its successive evolutions are methods currently applied in the peptide chemistry to remove the N-terminal amino acids from the peptidic chain (See ref. 30)

According to the more recent developments of the original procedure, the Edman degradation essentially consists in reacting a peptide containing terminal α-amino group(s) with a lower alkyl or aryl isothiocyanate (e.g. methylisothiocyanate, phenyl isothiocyanate, p-nitrophenylisothiocyanate and naphthylisothiocyanate) to form a thiocarbamyl-peptide derivative intermediate which is then submitted to cleavage of the terminal thiocarbamyl amino acid portion by cyclization to thiohydantoin derivative. This last step results in the selective elimination of the N-terminal amino acid(s) of the peptidic chain.

The Edman degradation procedure has been applied to aglucovancomycin and related antibiotics for the selective cleavage of the N-terminal amino acid, i.e. N-methyl-leucine (the first amino acid from the right-hand side), yielding a vancomycin hexapeptide derivative which is devoid of antibacterial activity (Ref. 31)

According to a preferred embodiment of this step ($c_1$), the double Edman degradation is carried out on the pentapeptide (IV) which has two N-terminal aminoacid moieties, by contacting the above mentioned pentapeptide (IV) with a 0.2–0.5 molar excess of methylisothiocyanate or phenylisothiocyanate, over the stoichiometric amount at a pH value between 8 and 9 in an aqueous solvent mixture (e.g. pyridine:water 1:1) at a temperature between 0° and 35° C., preferably at room temperature. The obtained bis-(methylthiocarbamyl) intermediate may be isolated from the reaction mixture according to common procedures and then submitted to double cleavage/cyclization without any further purification.

The cleavage/cyclization procedure involves heating the above intermediate in an acidic medium which does not affect the other essential portion of the molecule. For instance, this step may be suitably performed by dissolving the intermediate into trifluoroacetic acid and maintaining this solution at 40°–60° C. for a period of time which is sufficient to complete the reaction (HPLC control may be applied). In most cases, heating may not be necessary and the cleavage/cyclization reactions occur even at temperature comprised between 10° and 40° C.

The resulting reaction mixture is evaporated to dryness and then washed with a solvent which is capable of removing the thiohydantoin side product, or it is purified by method per se known in the art, e.g. by reverse-phase column chromatography. Usually, satisfactory results are obtained by applying the same conditions utilized for the purification of the pentapeptide (IV). By following this method the tetrapeptide (I) wherein $R_1$ is hydrogen, R and $R_0$ are amino is obtained as an acid addition salt with trifluoroacetic acid. This salt may be converted into the corresponding free base by neutralizing a water solution thereof. Salts of the tetrapeptide with bases or transformation into other acid addition salts may be achieved by means of the common procedures which are well known in the art.

If desired, the primary amino functions of the obtained tetrapeptide free base may be converted into protected amino groups by using the same protective reagents and methods described above. Analogously, a tetrapeptide of formula (I) wherein $R_1$ is hydrogen can be optionally transformed into the corresponding compound wherein $R_1$ represents a protecting group of the carboxylic function by means of known procedures such as those mentioned above.

Step ($b_2$):

The alternative process for the preparation of the tetrapeptides of general formula (I) starts with submitting the pentapeptide (III) to Edman degradation for the simultaneous elimination of the two amino acids bearing the substituents $X_1$ and $X_2$. The reaction conditions applied here are essentially the same as those described under step ($c_1$). In this case, being the resulting product (V) an intermediate compound to be used in the successive step of the process, it may not be necessary to apply extensive purification procedures to the crude reaction product besides washing it with solvents, e.g. diethyl ether, to remove the thiohydantoin side products.

Step ($c_2$):

Also in this case, as well as in step ($b_1$) of the other reaction pathway, one of the essential points of the procedure consists in the appropriate selection of the protecting groups. The same protecting groups, reagents and reaction conditions listed under the above description of step ($b_1$) can be applied here to the substrate (V). The selective protection of the amino and phenolic hydroxy groups (and, optionally, any other oxidation sensitive group) can be carried out simultaneously or in two separate stages. A two stage procedure is particularly preferred here since it allows to take advantage of the vicinity of the primary amino group and the hydroxymethyl rest by providing to this latter a temporary protection while performing the second protection stage (i.e. the protection of the phenolic hydroxy groups) under more drastic conditions. This approach permits to obtain a product to be submitted (after the removal of the intermediate protection of the hydroxymethyl group) to the successive oxidation, which shows a higher and more selective protection degree at the phenolic hydroxy groups than the one resulting from step ($b_1$). A practical procedure to provide a temporary protection of the hydroxy group of the hydroxymethyl moiety consists, for instance, in the formation of an oxazolidine intermediate involving both the hydroxy group of the hydroxymethyl moiety and the vicinal primary amino group (which has been previously protected, e.g. by means of a (lower alkoxy)carbonyl or phenyl-(lower alkoxy)carbonyl group).

According to this preferred procedure, the primary amino groups of the substrate (V) are protected, for instance, by a (lower alkoxy)carbonyl or a phenyl-(lower alkoxy)carbonyl radical, most preferably, a tert-butoxycarbonyl or benzyloxycarbonyl radical. The reaction conditions and the procedures for recovery and purification of the resulting products are essentially the same as those described for carrying out the protection of the amino groups in step ($b_1$). If necessary, a further purification can be performed by applying reverse-phase chromatography as described for the purification of the compounds of formula (IV) under the description of step ($b_1$) above.

The formation of the oxazolidine protecting group is usually carried out by contacting the above mentioned substrate of formula (V), protected on the amino groups, with an acetal or ketal, preferably a ketal from a $C_3$–$C_6$ aliphatic or $C_5$–$C_7$ alicyclic ketone and a lower alkanol, e.g. 2,2-dimethoxypropane or 1,1-dimethoxycyclohexane. The reaction is carried out in anhydrous conditions in the presence of an inert solvent, e.g. acetone, tetrahydrofuran, dioxane and the like and a catalytic amount of a strong acid, e.g. hydrogen chloride, concentrated sulfuric acid, p.toluenesulfonic acid, trifluoromethanesulfonic acid. The resulting reaction mixture, after neutralization, e.g. with sodium bicarbonate, is elaborated to yield the oxazolidine derivative wherein the oxazolidine ring incorporates both the primary hydroxy function and the protected (tert-butoxycarbonyl or benzyloxycarbonyl) amino group.

This intermediate oxazolidine product is then submitted to the further reactions for selectively protecting the phenolic hydroxy groups (and any other oxidation sensitive moiety, if necessary). The protecting groups and the suitable reagents for their introduction into the above mentioned substrate are essentially the same as those described for the protection of the phenolic hydroxy groups in step ($b_1$) above. Accordingly, the formation of lower alkyl, benzyl or benzoylmethyl ethers, optionally substituted as indicated above in the lower alkyl or phenyl portion and the formation of lower alkanol, benzoyl, lower alkoxycarbonyl and benzyloxycarbonyl esters are the preferred methods for providing the desired protection. The appropriate reactants and reaction conditions are essentially the same as those described for the protection of the phenolic hydroxy rests under step ($b_1$) above. Moreover, in this case a larger excess of the reagent(s) providing the protective groups may be employed and/or a wider temperature interval which may extend from 0° to 50° C. and/or a larger reaction time can be applied for obtaining a higher protection degree.

After completion of this stage, the temporary protection of the primary hydroxy group of the hydroxymethyl moiety is selectively removed to allow its conversion to carboxylic group by oxidation.

The removal of the oxazolidine protecting moiety may be carried out by acid hydrolysis at a temperature between 0° and 35° C. in an organic water miscible solvent such as, for instance, a lower alkanol, acetonitrile, tetrahydrofuran, dioxane and the like. The acid employed is preferably a diluted strong mineral acid, e.g. hydrochloric acid, hydrobromic acid and sulfuric acid. The above acidolytic conditions must be sufficiently mild to avoid the removal of the other protective groups previously introduced. The product obtained is recovered by common procedures and then utilized in the next oxidation reaction without any further purification. The oxidation of the substrate (V) selectively protected at the primary amino groups and the phenolic hydroxy groups (and, when needed, at other oxidation sensitive groups, apart from the primary hydroxy group of the hydroxymethyl rest), is carried out according to the same method described under step ($b_1$) above with potassium permanganate at basic or neutral pH or, preferably, with the Jones reagent.

It has been observed that with potassium permanganate, when the protection of the phenolic hydroxy rests is effected by formation of benzoylmethyl ethers, these protecting groups are, at least partially, oxidized and removed during the oxidation reaction. This problem may be kept under control by monitoring, e.g. by HPLC, the reaction mixture.

By using potassium permanganate at a pH value higher than 9, in the case of the presence of a lower alkyl ester group on the carboxylic function, a possible hydrolysis of said ester function may take place, thus re-generating the original fee carboxylic group. In this case, it is more suitable to use the Jones reagent.

When using the Jones reagent the oxidized product obtained corresponds to compound of formula (I) wherein both the primary amino groups and the phenolic hydroxy groups (and any other oxidation sensitive group which may have required protection) are still bearing their respective protecting groups. This product may be recovered and purified according to procedures per se known in the art, for instance, by reverse-phase column chromatography as described for the substrate (IV) under step ($b_1$) above or may be submitted to the deprotection stage without any further purification. The optional deprotection of the amino and phenolic hydroxy groups may be carried out in different stages, or simultaneously, depending on the type of protecting groups utilized and the degree of protection which is desired to be maintained in the final product (I). For instance, for the use of the compound (I) as precursor for the synthesis of new aglucodalbaheptides, it may be convenient to have the carboxylic function represented by the symbol Y in a protected form, e.g. as a carboxy ester. In such cases, when this group has been previously protected as an ester, it is necessary to carry out the deprotection of both the amino and the phenolic hydroxy groups under conditions which do not modify such ester function. In general, when the protection of the primary amino groups and of the phenolic hydroxy groups of the substrate (V) has been carried out in two stages, also the deprotection of these groups from the oxidized substrate (I) is carried out in two stages. For instance, the removal of the benzyloxycarbonyl groups from the phenolic hydroxy groups (and from any other group which has been protected in the same way) may be carried out by hydrogenolysis, e.g. by catalytic hydrogenation under the same conditions described under step ($c_1$) above, while the removal of the lower alkoxycarbonyl groups from the primary amino groups (and from any other group which has been protected in the same way) can be carried out by acid hydrolysis or solvolysis (e.g. in trifluoroacetic acid as described under step ($c_1$) above). When this stage is performed as the last stage of the process, it may be useful to recover the obtained product of formula (I), wherein both the amino and the phenolic hydroxy groups are deprotected, as an acid addition salt with the same acid utilized for the hydrolysis or solvolysis (e.g. with trifluoroacetic acid). This product may be purified or converted into the corresponding free base or into another acid addition salt by the same procedures mentioned under step ($c_1$) above. Also in this case, the tetrapeptide of formula (I) wherein $R_1$ represents hydrogen may be optionally transformed into the corresponding functional derivative wherein $R_1$ represents a protecting group by procedures per se known in the art. In the same way, when a product of formula (I) is obtained wherein R and $R_0$ each independently represent a free amino group, it may be transformed into the corresponding product of formula (I) wherein R and $R_0$ each independently represents a protected amino group by common procedures.

A specific example of the utilization of the tetrapeptides of this invention consists in their use for the preparation of synthetic aglucodalbaheptides of general formula (VI)

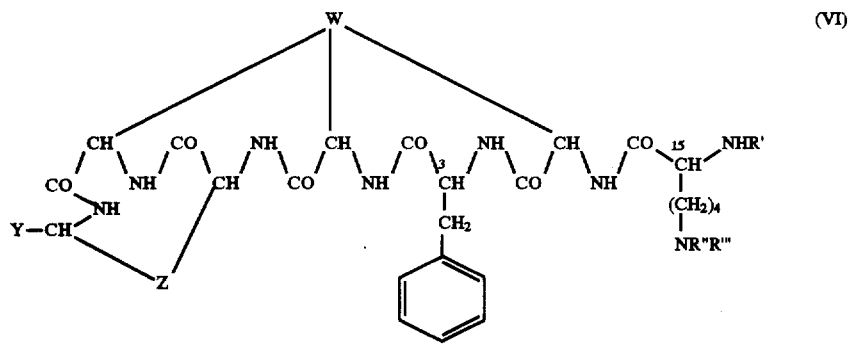

(VI)

wherein:

W and Z represent the relative portions of the aglycon of an antibiotic of the dalbaheptide group (aglucodalbaheptides);

Y represents a carboxylic group or a functional derivative of said carboxylic group;

R' and R", each independently, represent hydrogen or a protecting group of the amino function.

R'" represents hydrogen; and the salts of the above represented synthetic aglucodalbaheptides with acids or bases as well as their inner salts.

In the formula (VI) above and in the other related formulas the chiral center of each of the five basic aryl-and arylmethyl-amino acids of the aglucodalbaheptides has the same absolute configuration as that of the respective amino acid of the natural dalbapeptide from which the tetrapeptide starting material (I) has been obtained.

The chiral centers which are synthetically introduced into the aglucodalbaheptides of formula (VI) and are indicated with the index 3 and 15, respectively, may have both R and S absolute configuration, depending on the absolute configuration of the amino acid which is inserted.

However, according to a preferred embodiment of this process, the configuration of the introduced chiral center identified with the index 3 is S, while the configuration of the chiral center identified with the index 15 may be both R and S, most preferably, R.

A most preferred group of aglucodalbaheptide antibiotics of formula (VI) comprises those derivatives of formula (VIa)

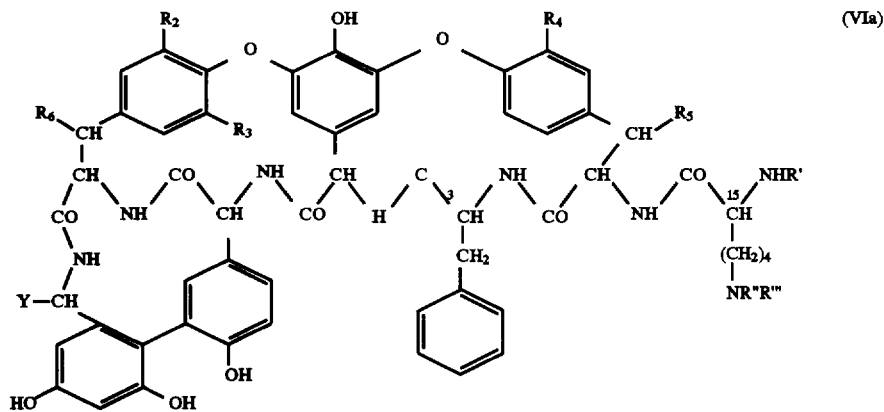

(VIa)

wherein:

Y represents a carboxylic group or a lower alkyl ester derivative of said carboxylic group;

R' and R", each independently, represent hydrogen or a protecting group of the amino function, preferably, hydrogen;

R'" represents hydrogen;

$R_2$ represents hydrogen;

$R_3$ and $R_4$, each independently, represent hydrogen or chloro;

$R_5$ represents hydrogen or hydroxy, preferably, hydrogen;

$R_6$ represents hydrogen or hydroxy;

and their salts with acids and bases, preferably, their salts with the pharmaceutically acceptable acids and bases, as well as their inner salts.

The process for the manufacture of the aglucodalbaheptide antibiotics of formula (VI) is running through the following Reaction Scheme 3.

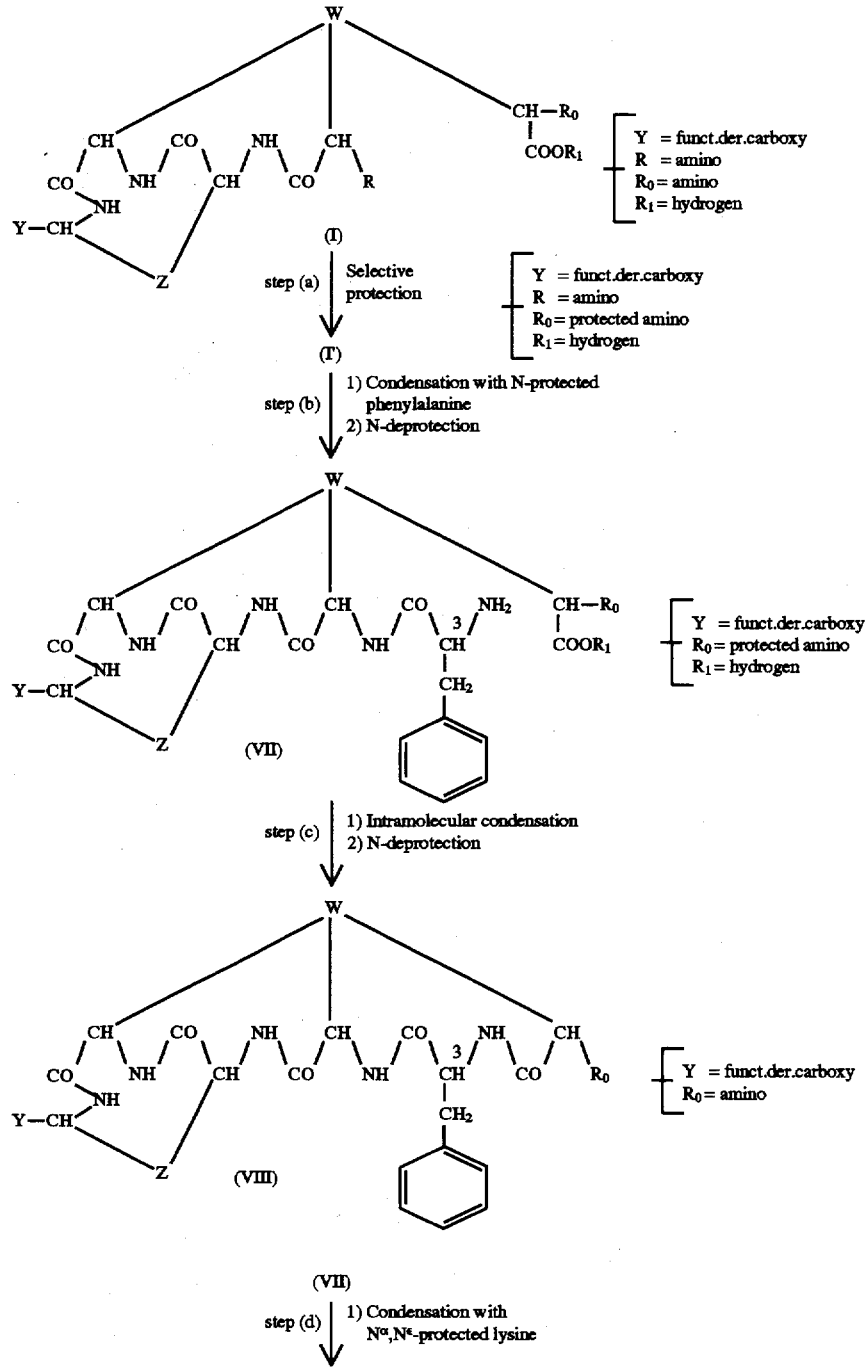

Reaction Scheme 3

-continued
Reaction Scheme 3

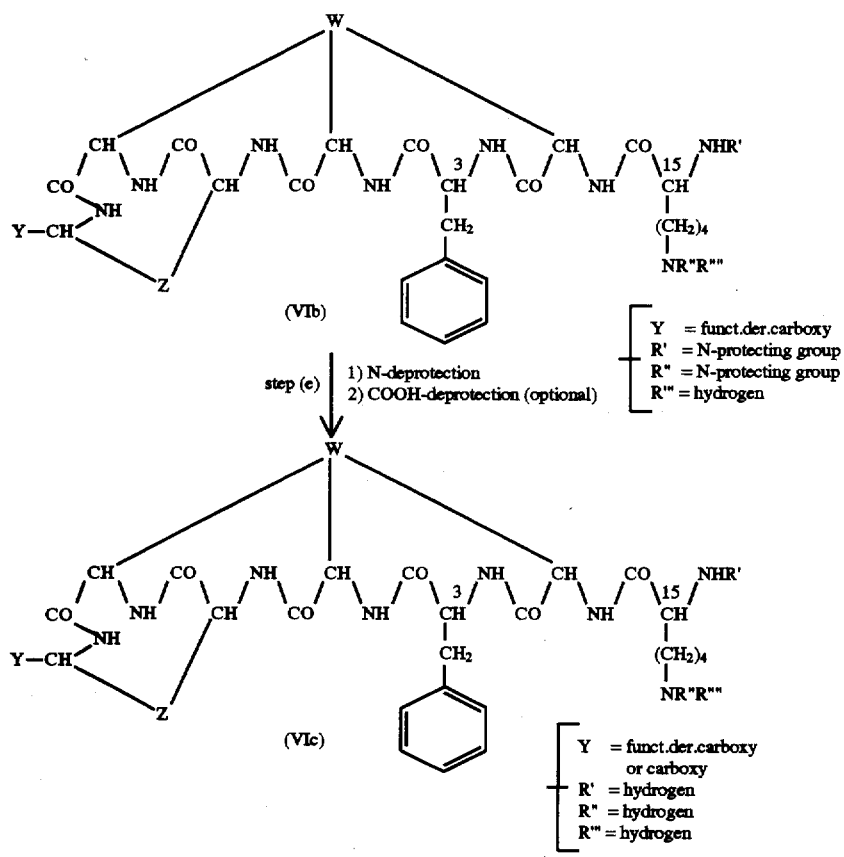

In the above Reaction Scheme the symbols W and Z have the same meanings as above while the term "funct. der. carboxy" relative to the meaning of the symbol Y means that such symbol represents a functional derivative of the carboxylic group as described before, including a protected carboxylic group which can be deprotected at the end of the process.

The first step(a) of the above reaction scheme involves the selective protection of the amino group represented by the symbol $R_0$ in the tetrapeptide of formula (I) to yield the tetrapeptide of formula (I').

Said selective protection may be accomplished, for instance, by protecting first the more reactive amino group identified with the symbol R in the tetrapeptide of formula (I), then, protecting the amino group represented by the symbol $R_0$ with a different type of protecting group which is not cleaved under the conditions required for the subsequent elimination of the protection (deprotection) of the amino group identified with the symbol R.

This last operation leads to a tetrapeptide compound (I') wherein $R_0$ is a protected amino group and R is a free amino group apt to react with the selected amino acid derivative, that is, N-protected phenylalanine, to form a pentapeptide according to reaction step(b). This step is completed by the elimination of the N-protecting group originating from the N-protected phenylalanine precursor, thus yielding the pentapeptide of formula (VII).

The performance of the above described reaction step (b), involves the application of reaction conditions where the presence of a free carboxy group in the position Y would negatively affect the reaction course. Therefore, it is preferred to use a tetrapeptide derivative (I') wherein Y represents a functional derivative of said carboxylic group to avoid any undesired interference of the free carboxylic group when the condensation conditions are applied for the coupling of the N-protected phenylalanine with the tetrapeptide (I') to form the pentapeptide (VII).

For analogous reasons, it is preferred to maintain the protection of the carboxy group represented by the symbol Y also in the successive steps involving the formations of other peptidic bonds.

In the performance of the above mentioned reaction steps as well as in the successive reactions it is not necessary to provide protection to the phenolic or benzylic hydroxy groups which may be contained in the portion W and Z of the tetrapeptide and pentapeptide. However, if these protecting groups are originally present in the tetrapeptide of formula (I), they may be maintained during all the successive reaction course and may be optionally cleaved at the end of the whole process, when the aglucodalbaheptide (VIb) or (VIc) is obtained.

The successive step(c) involves an intra-molecular condensation between the free amino group of the pentapeptide (VII) and the carboxylic rest $COOR_1$ wherein $R_1$ is hydrogen. Also in this case the reaction course would be negatively affected by the presence of an additional free carboxylic group in the position Y of the pentapeptide. In fact, such additional carboxylic group would take part to intermolecular coupling reactions with the free amino group yielding undesired side-products. Therefore, in this case it is particularly important to maintain the protection of such carboxylic group as described above. The step (c) includes also the N-deprotection of the amino group represented by the symbol $R_0$ to form the intermediate hexapeptide of formula (VIII).

The following step(d) involves the addition of the second amino acid by condensation with a $N^\alpha,N^\epsilon$-protected lysine derivative, to yield the aglucodalbaheptide derivative (VIb) which, in the successive step(e), can be submitted to the N-deprotection of the amino groups of the lysine moiety and, if desired, when Y is an easily cleavable protected carboxy group, to the cleavage of such protected carboxy group, to yield the aglucodalbaheptide (Ic).

In the following description are given more specific details on the way each step of the above described process may be carried out.

Step (a):

The crucial point for the performance of this step is the selection of a reagent suitable for introducing a protecting group of a primary amino function which preferentially reacts with the amino group represented by the symbol R in formula (I).

With respect to this desired effect, it has been found that satisfactory selectivity and yields are obtained by employing di-tert-butyldicarbonate as the reagent furnishing the N-protecting group.

This reagent is contacted in an about equimolecular amount with the tetrapeptide of formula (I) in a solution consisting of a mixture of water and an inert water miscible organic solvent preferably selected from lower alkanols, acetone, tetrahydrofuran, dioxane and dimethoxyethane at a temperature between −5° and 20° C., preferably, between 0° and 10° C. at a pH between 6 and 8, preferably between 6,5 at 7,5.

The proportion between water and organic solvent is varying between 1:9 and 9:1, preferably between 4:6 and 6:4.

The desired product of formula (I) wherein R is a tert-butoxycarbonylamino group (all other symbols being as indicated in the Reaction Scheme 3) is usually obtained together with some amounts of a side-product wherein both R and $R_0$, are tert-butoxycarbonylamino rests.

The side-product can be easily separated from the desired mono-protected product, for instance, by extraction of an acid aqueous mixture containing both products with a water immiscible solvent.

The recovered side-product can be converted to the unprotected starting material by means of acid hydrolysis (e.g. with trifluoroacetic acid). The regenerated starting material, in turn, is reacted again with di-tert-butyldicarbonate under the above described conditions. If needed, the regenerating process of the side-product material followed by reaction with di-tert-butyldicarbonate can be repeated two or three times in order to obtain a high conversion yield of the desired mono-protected product.

The mono-protected product is then submitted to a further intermediate process for protecting the free amino group represented by the symbol $R_0$ with a protecting group which is not cleaved under the acidic treatment conditions which are required to remove the tert-butoxycarbonyl group. Reagents that can be used to achieve the above desired effect may be selected from those forming carbamate derivatives.

Examples of such reagents and the relative reaction conditions are described, for instance, in the book by T. W. Greene and P. G. M. Wuts: "Protective Groups in Organic Synthesis" second edition, J. Wiley, N.Y., 1991 (see, in particular, pages 315–348).

Accordingly, the following protecting groups are particularly suitable for the protection of the amino group identified with the symbol $R_0$ in the tetrapeptide of formula (I'): 9-fluorenylmethoxycarbonyl, 9-(2-sulfo)fluorenylmethoxycarbonyl, 9-(2,7-di-bromo)fluorenylmethoxycarbonyl, 2,7-di-tert-butyl[9-(10,10-dioxo-thioxanthenyl)] methoxycarbonyl, 1,1-dimethyl-2,2-dibromoethoxycarbonyl, 1,1-dimethyl-2,2,2-trichloroethoxycarbonyl, allyloxycarbonyl, benzyloxycarbonyl, p-nitrobenzyloxycarbonyl, p-bromobenzyloxycarbonyl, 2,4-dichlorobenzyloxycarbonyl and 4-methylsulfinylbenzyloxycarbonyl.

According to a preferred embodiment of this invention, the benzyloxycarbonyl radical is employed as protecting group of the amino function represented by the radical $R_0$ in formula (I). For this purpose, the above mentioned mono-protected tetrapeptide of formula (I) wherein R represents a tert-butoxycarbonylamino rest is reacted with a suitable reagent capable of introducing such benzyloxycarbonyl group on the amino function, for example, benzylchloroformate in the presence of an excess of a mild base, e.g. sodium bicarbonate, potassium bicarbonate, or a tri-(lower alkyl amine).

The reactant providing the N-protecting group is usually employed in an equimolecular amount with respect to the tetrapeptide. However, in certain cases it may be necessary to employ a slight molecular excess (up to 20 percent) of such reagent to complete the reaction.

The reaction is usually carried out in the presence of a solvent preferably consisting of a mixture of water and a water miscible inert organic solvent, such as those described above for the introduction of the tert-butoxycarbonyl rest. The two reactants are employed in about equimolecular amounts and the reaction temperature is maintained between 0° and 50° C., preferably between 15° and 30° C. The di-protected tetrapeptide obtained according to the above procedure is then submitted to acidic treatment suitable for the selective removal of the tert-butoxycarbonyl group.

Such treatment consists, for instance, of contacting the di-protected tetrapeptide with an excess of dry trifluoroacetic acid at a temperature between 5° and 30° C. for 5 to 25 minutes.

The tetrapeptide of formula (I') wherein $R_0$ is a benzyloxycarbonylamino rest (all other symbols being as in Reaction Scheme 3) is then recovered from the reaction medium according to procedures per se known in the art.

Step(b):

This step consists in reacting the N-protected tetrapeptide of formula (I') with a suitable derivative of phenylalanine. Such derivative must be protected on the amino group and must contain an activating group of the carboxy rest suitable for promoting the condensation process. The protecting group of the amino rest of the phenylalanine must be different from that of the $R_0$ portion of the tetrapeptide, since it must be removed in the next step under conditions which do not affect such $R_0$ portion.

A solution of this problem consists in empoying a carbamate forming group which can be cleaved under the same conditions which have been applied in the former step (a). The tert-butoxycarbonyl rest is, therefore, one of the preferred N-protecting groups for the phenylalanine.

The activating group of the N-protected phenylalanine carboxylic function may be selected from those forming the usual activated ester moieties.

Examples of activated esters are those described in general terms as amino acid esters for peptide coupling in the book by L. F. Fieser and M. Fieser, "Reagent for organic Synthesis" J. Wiley, New York.

Activated esters forming reagents which can be used to activate the carboxy function of the N-protected phenylalanine are for instance those described by R. Schwyzer et al. in Helv. Chim. Act., 1955, 38, 69–70 and include the following:

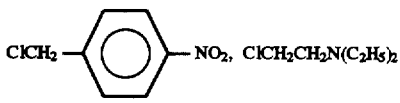

Other activating groups of the carboxylic function of the N-protected phenylalanine that can be emlpoyed according to the process of this invention are the following:

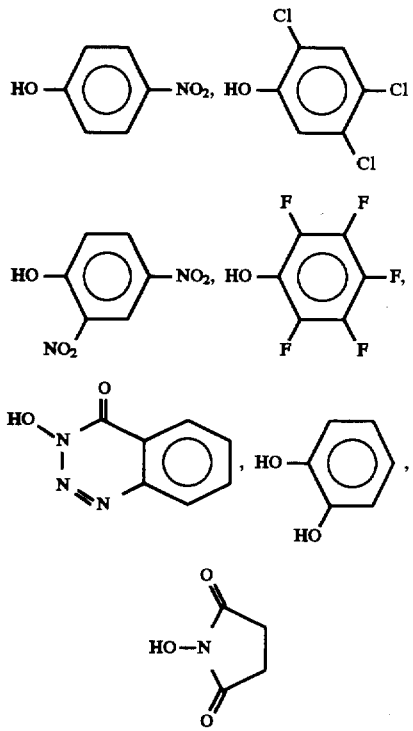

as described by J. Jones in "The Chemical Synthesis of Peptides", pages 55–58, Clarendon Press-Oxford (1991)

According to one preferred embodiment of this invention the ester of N-protected phenylalanine with N-hydroxysuccinimide is employed for the condensation reaction with the tetrapeptide of formula (I').

The condensation reaction is carried out under the general conditions required for the formation of polipeptides. Usually, the two reactants are contacted in about equimolecular amounts (in the presence of an about equimolecular amount of an organic tertiary amine, e.g. a tri-lower alkyl amine, if the amino group R of the compound (I') is in the form of an acid addition salt) in an organic inert solvent at a temperature between 5° and 35° C., preferably between 15° and 25° C. The organic inert solvent is usually selected from organic amides, (e.g. dimethylformamide), polyethers (e.g. dimethoxyethane), cyclic ethers (e.g. tetrahydrofuran), esters (e.g. ethyl acetate) and dimethylsulphoxide. A preferred solvent is dimethylformamide.

The di-protected pentapeptide derivative which forms following the condensation reaction is then treated under conditions promoting the cleavage of the N-protected amino group of the phenylalanine residue without affecting the N-protected amino group $R_0$, thus yielding the pentapeptide of formula (II). In the case where the amino group of phenylalanine is protected through the formation of a tert-butylcarbamate and $R_0$ is benzyloxycarbonylamino the preferred treatment is essentially the same as that applied at the end of step (a) for the removal of the protecting tert-butoxycarbonyl group of the R amino moiety of the corresponding tetrapeptide.

Step(c):

The mono protected pentapeptide (VII) resulting from the previous reaction is submitted to intramolecular condensation for the formation of a peptidic bond between the free amino group of the phenylalanine rest and the carboxylic group $COOR_1$ wherein $R_1$ is hydrogen.

The intramolecular condensation apparently occurs only under well defined conditions by selecting appropriate condensing agents, solvents, reagents proportions and temperature. The intramolecular reaction occurs via activation of the carboxylic group $COOR_1$ of the pentapeptide of formula (VII) by reaction with N-hydroxybenzotriazole in the presence of dicyclohexylcarbodiimide. The conditions for the formation of the activated carboxy derivative of the pentapeptide require that the carboxy group $COOR_1$ is first salified with an organic tertiary amine such as diethylamine, N-methylpyrrolidine, N-methylpiperazine or N-methylmorfoline before reacting with N-hydroxybenzotriazole. The pentapeptide, the organic amine and the N-hydroxybenzotriazole are employed in about equimolecular amounts while the dicyclohexylcarbodiimide is employed in a 10 to 20 percent molar excess. The reaction is preferably carried out in a solvent mixture consisting of dimethylformamide and dichloromethane in about equal volumes. The temperature of the reaction mixture is kept between 10° and 35° C. for a sufficient period of time to complete the intramolecular condensation. The time required may be determined by following the reaction course with the usual analytical systems which include TLC and HPLC methods.

The solid recovered from this reaction may be purified by reverse phase column chromatography, for instance, on silica-gel by using a linear gradient of from 10 to 70 per cent of acetonitrile in water and checking the collected fraction by HPLC: The fractions containing the pure N-protected hexapepetide are combined and, after concentration, the product is precipitated by addition of a non-solvent (e.g. diethyl ether). Inorganic impurities which may be present in the precipitated product may be eliminated by adding the product to dimethylsulfoxide, filtering the suspension and lyophilizing the clear filtrate.

The N-protected hexapepetide is then transformed in the hexapepetide compound of formula (VIII) by removal of the protecting group of the amino moiety identified by the radical $R_0$. Said protecting group may be eliminated by applying the appropriate methods suggested by the specific literature regarding the N-protecting groups mentioned above. When the N-protecting group of the amino function identified by the radical $R_0$ is a benzyloxycarbonyl group, the removal of such protecting group is usually carried out by catalytic hydrogenation at atmospheric pressure and room temperature, in the presence of an organic solvent or a mixture of organic solvents and, preferably, an aqueous mineral acid (e.g. 1N HCl). In such case, the hexapepetide of formula (VIII) is recovered from the filtered hydrogenated solution as the salt with said mineral acid.

Step (d):

The hexapepetide of formula (VIII) of step (c) is condensed with a $N^\alpha,N^\varepsilon$-protected lysine derivative activated on the carboxylic group. For both the N-protection and the activation of the carboxylic group of the lysine the same reagents that are employed for N-protection and carboxy-activation of phenylalanine in step (b) can be utilized. The reaction conditions and the mutual proportions of the reagents and the recovery procedure are essentially the same as in the case mentioned above.

The result of this condensation is an aglucodalbaheptide of formula (VIb) wherein each of the two amino groups of the lysine portion bears an N-protecting group.

Step (e):

This step is primarily performed for removing the two N-protecting groups of the aglucodalbaheptide (VIb). There is no special problem for this removal. In particular, when such N-protecting groups are tert-butoxycarbonyl rests, the removal is carried out with essentially the same treatment with trifluoroacetic acid as described for the removal of the tert-butoxycarbonyl rest from the phenylalanine moiety of the pentapeptide obtained in step(c). The aglucodalbaheptide (VIc) may be obtained from the above treatment as a free base if the residual of the evaporated trifluoroacetic acid solution is treated with an aqueous alkali solution at a pH 8.5. The free base of the aglucodalbaheptide may be further purified by reverse phase column chromatography by using essentially the same procedure and conditions applied in step (c) for the purification of the hexapeptide of formula (VIII).

easily cleavable under mild conditions, such function is maintained unmodified in the final compound which, however, is still part of this invention.

An aglucodalbaheptide (VIc) having a carboxylic group as substituent Y can be transformed into an aglucodalbaheptide derivative of formula (VIc) wherein Y is a functional derivative of such carboxylic function (e.g. an ester or an amide) as described above. Methods for the preparation of such functional derivatives from the corresponding free carboxylic compound are widely described in the dalbaheptides literature. In particular, see the following patent applications: EPA Publication Nos. 216775, 340245, 370283, 376041, 351685, 460448, and International Application Publication No. WO93/0360.

In a specific representative example embodying the performance of the Reaction Scheme 3 above, the tetrapeptide of formula (I) derived from aglucoteicoplanin (see example 7a) has been employed as the starting material. Said tetrapeptide has the following structure formula

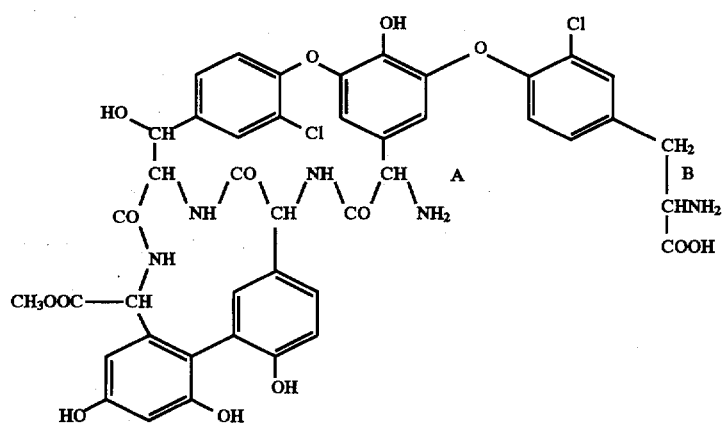

The aglucodalbaheptide of formula (VIc) wherein Y represents a protected carboxylic function, if desired, may be converted to the corresponding free carboxy derivative by removal of the protecting group.

For instance, when the protected carboxylic function is an ester with a lower alkanol, the hydrolysis of such ester may be performed by suspending the product in tetrahydrofuran and adding a molar excess (10–50%) of 1N NaOH at room temperature. The above conditions do not affect the other portions of the molecule.

When the substituent Y of the aglucodalbaheptide (VIc) is a functional derivative of the carboxylic group which is not and is currently indicated in the following description and in example 14 as ATTP methyl ester. For the purpose of clarity and better understanding of the examples which follow this description, in the above formula the nitrogen atoms of the two different free amino groups have been distinguished with the letter A and B, respectively.

By following the multi-step process of Reaction Scheme 3 described above and employing the appropriately protected amino acids L-phenylalanine and D-lysine in steps (b) and (d), respectively, the following compound falling into general formula (VIc) has been obtained

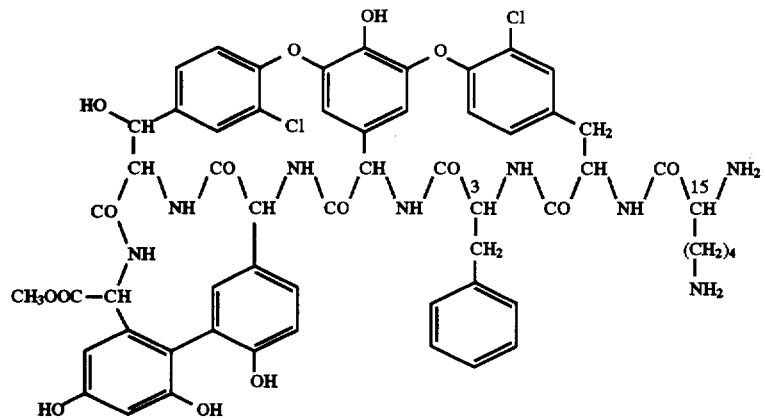

wherein the chirality centers identified with the indexes 3 and 15 have respectively S and R absolute configuration.

This reaction process runs through the preparation of the corresponding pentapeptide and hexapepetide intermediates of formula (VII) and (VIII) which are conventionally identified as $N^B$-protected-(L-phenylalanyl)$^3$-ATPP methyl ester and (L-phenylalanyl)$^3$-ATHP methyl ester, respectively.

The above compound has been conventionally named (L-phenylalanyl)$^3$-(O-lysyl)$^{15}$-aglucoteicoplanin dalbaheptide methyl ester [(L-phenylalanyl)$^3$-(D-lysyl)$^{15}$-ATDH methyl ester] where the apexes 3 and 15 indicate that the amino acid units containing the carbon atoms numbered as 3 and 15 in the aglucoteicoplanin basic skeleton according to A. Malabarba et al. J. Antibiotics 42, 1684–1697, (1989) are replaced by a L-phenylalanine and a D-lysine rest, respectively. The absolute configuration of the chirality centers identified with the index 3 and 15 is S and R, respectively, as described above.

This compound shows a remarkable antimicrobial activity in in vitro experiments as reported in the following TABLE I wherein teicoplanin and teicoplanin aglycon are taken as the reference compounds.

TABLE I

| (L No.) | Strain | (L-phenyl-alanyl)$^3$-(D-lysyl)$^{15}$-agluco-teicoplanin dalbaheptide methyl ester | teico-planin | teico-planin aglycon |
|---|---|---|---|---|
| (165) | Staph. aureus Tour | 0.13 | 0.13 | 0.13 |
| (819) | S. aureus Smith | 0.13 | 0.25 | 0.06 |
| (561) | S. aureus clin. isol. | 0.06 | 8 | 0.13 |
| (147) | S. epidermidis ATCC 12,228 | 0.13 | 8 | 0.06 |
| (533) | S. epidermidis clin. isol. | 0.13 | 8 | 0.016 |
| (602) | S. haemolyticus clin, isol. | 0.5 | 32 | 0.25 |
| (49) | Strep. pyogenes C203 | 0.25 | 0.13 | 0.13 |
| (44) | Strep. pneumoniae UC41 | 0.13 | 0.13 | 0.13 |
| (149) | Enterococcus faecalis ATCC 7,080 | 0.5 | 0.13 | 0.13 |
| (502) | E. faecalis clin. isol. | 16 | >128 | >128 |

The in vitro antibacterial activity of the compounds is determined by means of standard agar-dilution tests in microtiter. Iso-Sensitest broth (Oxoid) is used for all bacteria except streptococci (Todd-Wewitt broth, Difco) and enterococci (Mueller-Hinton, Difco). Broth cultures are diluted so that the final inoculum is about $5\times10^5$ cfu/ml (colony forming units per ml). All broth microdilution MICs are performed in the presence of 0.01% bovine serum albumin (Pentax fraction V, Sigma). MIC (minimal inhibitory concentration) is considered as the lowest concentration which shows no visible growth after incubation at 37° C. for 18–24 hours.

The above synthetically obtained aglucodalbaheptide, while maintaining substantially the same level of activity as the teicoplanin aglycon against most of the bacteria which are usually sensitive to the dalbaheptides, is surprisingly active also against a clinical isolate of Enterococcus faecalis which is resistant to both teicoplanin and teicoplanin aglycon.

By using the process of this invention and selecting as starting materials other tetrapeptide compounds of this invention a series of synthetic aglucodalbaheptides of formula (VI) can be obtained.

The compounds of formula (VI) can be employed as the active ingredients of the antimicrobial preparations used in human and veterinary medicine for the prevention and treatment of infectious diseases caused by pathogenic bacteria which are susceptible to said active ingredients, in particular, for the treatment of infections caused by Enterococci, Streptococci and Staphylococci strains.

The compounds of the present invention can be administered orally, topically or parenterally, the parenteral administration route being preferred.

Depending on the route of administration, these compounds can be formulated into various dosage forms.

Preparations for oral administration may be in the form of capsules, tables, liquid solutions or suspensions. As known in the art, the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations, generally in the form of aqueous or oily solutions or suspensions, may contain conventional additives such as suspending agents.

For topical use the compounds of the present invention may also be prepared in suitable forms for absorption through the mucous membranes of the nose and throat or bronchial tissues and may conveniently take the form of liquid sprays or inhalants, lozenges, or throat paints.

For medication of the eyes or ears, the preparation may be presented in liquid or semi-liquid form. Topical applications may be formulated in hydrophobic or hydrophilic bases as ointments, creams, lotions, paints, or powders.

For rectal administration the compounds of the invention are administered in the form of suppositories admixed with conventional wehicles, such as, for example, cocoa butter, wax, spermaceti or polyethylenglycols and their derivatives.

Compositions for injection may take such forms as suspensions, solutions, or emulsions in oily or aqueous vehicles, and may contain formulatory agents such as suspending, stabilizing and/or dispersing agents.

Alternatively, the active ingredient may be in powder form for reconstitution at the time of delivery with a suitable vehicle, such as sterile water.

The amount of active principle to be administered depends on various factors such as the size and conditions of the subject to be treated, the route and frequency of administration, and the causative agent involved.

The compounds of the invention are generally effective at a dosage comprised between about 1 and about 40 mg of active ingredient per Kg of body weight. Depending on the characteristics of the specific compound, the infection and the patients, the effective dose can be administered in a single administration per day or divided in 2 to 4 administrations per day. Particularly desirable compositions are those prepared in the form of dosage units containing from about 30 to about 500 mg per unit.

EXAMPLES

The analytical methods and procedures utilized for the characterization of the compounds prepared according to the following examples 1–13 are described in a separate paragraph following this series of examples.

Example 1: Preparation of the Pentapeptide Derivative from Reductive Cleavage of Deglucoteicoplanin (Step (a))

Method A:

A suspension of 19 g (about 10 mmol) of teicoplanin $A_2$ complex in 600 ml of a mixture $H_2O$/ethanol 65/35 is stirred at 10°–15° C. for 90 min, while adding portionwise 40 g of $NaBH_4$ pellets. A clear solution forms which is stirred at room temperature for 5 hours then it is diluted with 1 liter of MeOH and 0.5 l of EtOH and slowly poured into a solution of 100 ml of acetic acid in 0.5 l of MEOW. The solvents are evaporated at 35° C. under reduced pressure and the jelly residue is redissolved in 1 liter of $H_2O$. The resulting solution is loaded at the top of a column of 200 g of silanized silica-gel in $H_2O$. After eluting with 2 l of $H_2O$, the column is developed with a linear step gradient from 10% to 80% of $CH_3CN$ in 0.01N acetic acid, in 15 hours at the flow rate of 400 ml/h while collecting 25 ml fractions.

The fractions containing pure product are pooled and the solvents are evaporated, at 40° C. under reduced pressure, in the presence of butanol to avoid foaming. The solid residue is collected, washed with 200 ml of diethyl ether and dried at room temperature in vacuo for 3 days to give 16 g (about 80% yield) of the pentapeptide of the reductive cleavage of teicoplanin $A_2$ complex.

This product is suspended in 850 ml of 2,2,2-trifluoroethanol and dry HCl is bubbled at 70° C. into the suspension while stirring for 16 hours. The insoluble product is then collected and dissolved in a sufficient amount of $H_2O$/ethanol 65/35 which is loaded at the top of a column of 200 g of silanized silica-gel in $H_2O$. The column is eluted with 2 l of $H_2O$ and then developed with a linear step gradient from 10% to 80% of $CH_3CN$ in $H_2O$ in 15 hours at the flow rate of 400 ml/h while collecting 25 ml fractions. The fractions containing pure products are pooled and the solvents are evaporated at 40° C. under reduced pressure. The solid residue is collected and dried in vacuo to give 3.5 g of the compound of the title in a total yield of 25% from teicoplanin $A_2$ complex (HPLC, method a: $t_R$ 11.6 minutes)

Method B:

A suspension of 13 g (about 10 mmol) of deglucoteicoplanin in a mixture $H_2O$:ethanol 65:35 (600 ml) is stirred at 10°–15° C. for 90 min, while addding portionwise 100 g of $NaBH_4$ pellets. The solution which forms is stirred for 16 hours and then handled as in the first part of Method A above. In this case, 200 ml of acetic acid is employed to destroy the $NABH_4$ excess.

After chromatography on silanized silica gel the eluted fractions containing pure product are pooled and evaporated to give 3.7 g of the compound of the title in a 27% yield from deglucoteicoplanin.

Example 2: Protection of the Amino Functions of the Compound of Example 1 with the Tert-Butoxycarbonyl Group (Step ($b_1$))

To a stirred solution of 24 g (about 20 mmol) of the pentapeptide derivative of Example 1 in 400 ml of a mixture dioxane-water 1:1 (v/v), 20 ml of a 1M aqueous solution of sodium bicarbonate is added followed by a solution of 9 g (about 48 mmol) of di-tert-butyl-dicarbonate in 100 ml of a mixture dioxane-water 1:1 (v/v). The reaction mixture is stirred at room temperature for 5 hours, then, it is diluted with 250 ml of water. The resulting solution is adjusted at pH 4 with 1N HCl and extracted with ethyl acetate (2×200 ml). The organic layer is separated, washed with water (2×100 ml), dried over sodium sulfate, then it is concentrated at room temperature under reduced pressure to a small volume (about 58 ml). On adding 450 ml of diethyl ether, a solid separates which is collected by filtration to yield 27 g (about 95%) of the title compound. (HPLC, method b: $t_R$=11.3 minutes)

Example 2(a): Protection of the Carboxylic Group of the Compound of Example 2 (Step ($b_1$))

To a stirred solution of 30 g (about 22 mmol) of the compound of Example 2 in 220 ml of dimethylformamide, 2.5 g (about 23 mmol) of potassium bicarbonate is added, followed by a solution of 22 ml (about 23 mmol) of methyl iodide in 30 ml of dimethylformamide. After stirring at room temperature for 24 hours, the reaction mixture is poured into 1 l of water. The resulting cloudy solution is adjusted at pH 3 with 1N HCl and extracted with 1 l of a ethyl acetate:1-butanol 1:1 (v/v) mixture. The organic layer is separated, washed several times with water until the aqueous washings possess neutral pH, then it is concentrated at 40° C. under reduced pressure to a small volume. On adding a large excess of diethyl ether a solid precipitate is obtained which is collected and dried in vacuo at room temperature overnight yielding 30 g of pure title compound (HPLC, method b: $t_R$=16.1 minutes).

Example 3: Protection of the Phenolic Hydroxy Groups of the Compound of Example 2 with Benzyloxycarbonyl Groups (Step ($b_1$))

To a stirred solution of 5.6 g (about 4 mmol) of the compound of Example 2 in 200 ml of an anhydrous mixture dimethylsulfoxide:tetrahydrofuran 4:1 (v/v), 11 g (about 80 mmol) of potassium carbonate and 11 ml (about 80 mmol) of triethylamine are added at room temperature. The resulting suspension is stirred at room temperature for 1 hour, then it is cooled to 15° C. and a solution of 7.5 ml (about 53 mmol) of benzyl chloroformate in 20 ml of dry tetrahydrofuran is added dropwise in 30 minutes. After stirring at room temperature overnight, the reaction mixture is poured into 1.8 l of a stirred mixture water:ethyl acetate:acetic acid (glacial) 49:49:2 (v/v/v). The organic layer is separated, dried over sodium sulfate, then the solvent is evaporated at room temperature under reduced pressure to give an oily residue which solidifies by slurring with diethyl ether. The solid thus obtained is collected to give 6.6 g of a mixture of at least five products (HPLC), corresponding to the title compound with different degrees of protection at the phenolic hydroxy groups.

This product is suitable for the next oxidation step. (HPLC, method c: $t_R$=15.9, 19.0, 26.2, 29.8, 32.3 minutes)

Example 3(a): Protection of the Phenolic Hydroxy Groups of the Compound of Example 2(a) with Benzyloxycarbonyl Groups (Step ($b_1$))

To a stirred solution of 30 g (about 21 mmol) of the compound of Example 2(a) in 900 ml of a dioxane:water 1:1 (v/v) mixture, 21 g (about 65 mmol) of cesium carbonate is added. After stirring at room temperature for 30 minutes, a solution of 18 ml (about 130 mmol) of benzyl chloroformate in 50 ml of dioxane is added dropwise, then the reaction mixture is stirred at room temperature for additional 18 hours. Afterwards, the reaction mixture is poured into 1.5 l of a stirred mixture ethyl acetate:water 1:1 (v/v) acidified at pH 3 with 1N HCl and the organic layer is separated and worked up as described above in Example 3, yielding 36 g of the title compound as a mixture of products with different degrees of protection at the phenolic hydroxy groups, as above described in Example 3. (HPLC, method c: $t_R$=25.5, 28.8, 29.2, 30.3, 32.5 minutes)

Example 4: Oxidation of the Compound of Example 3 to the Corresponding Acid (Step ($b_1$))

The Jones reagent, "standard solution", is prepared according to the procedure described in Fieser & Fieser "Reagents for Organic Synthesis", Vol. 1: pag.142, John Wiley & Sons, Inc., New York (1967).

To a stirred solution of 6 g of the product of Example 3 in 90 ml of tetrahydrofuran, 21 ml of a "standard solution" of Jones reagent is added dropwise, in 1.5 hours, while maintaining the temperature between 20° C. and 25° C. After 30 minutes, the reaction mixture is poured into 800 ml of a mixture water:ethyl acetate 1:1 (v/v), under vigorous stirring. The organic layer is separated, washed several times with a 1N aqueous solution of sodium metabisulfite until peroxides are completely decomposed, afterwards it is dried over sodium sulfate and concentrated to a final volume of about 50 ml. On adding 450 ml of diethyl ether, a solid separates which is collected by filtration to yield 5.7 g of the title compound as a mixture of at least three main reaction products (HPLC). The crude reaction mixture (containing also about 30% of unreacted material, probably protected at the primary hydroxymethyl group as well) is submitted to the catalytical hydrogenation step without any further purification. (HPLC, method c: $t_R$=18.0, 21.5, 24.7 minutes)

Example 4(a): Oxidation of the Compound of Example 3(a) to the Corresponding Acid (Step ($b_1$))

By following the same procedure as that described in Example 4, starting from 36 g of the compound of Example 3(a), 34.3 g of the title compound are obtained. (HPLC, method c: $t_R$=19.7, 22.3, 25.8 minutes).

Example 5: Removal of the Benzyloxycarbonyl Protecting Groups from the Compound of Example 4 (Step ($b_1$))

A solution of 5 g of the above crude product in 200 ml of a mixture methanol:dimethylformamide:acetic acid (glacial) 5:2:2 (v/v/v) is hydrogenated (1 atm, 25° C.) in the presence of 2.5 g of 5% Pd/C. About 300 ml of hydrogen is absorbed within 2 hours, afterwards the catalyst is filtered off. Methanol is evaporated at room temperature under reduced pressure and the remaining solution is poured into 500 ml of water. The resulting cloudy solution is extracted with 500 ml of n-butanol. The organic layer is separated, washed with 500 ml of water, then it is concentrated at 45° C. under reduced pressure to a final volume of about 30 ml. On adding 200 ml of diethyl ether a solid separates which is collected by filtration, washed with 100 ml of diethyl ether, and then dried at room temperature in vacuo overnight to give 3.2 g of a crude product containing (HPLC) about 60% of the title compound which is still protected by tert.butoxycarbonyl groups on the amino functions. (HPLC, method b: $t_R$=6.0 minutes)

Example 5(a): Removal of the Benzyloxycarbonyl Protecting Groups from the Compound of Example 4(a) (step ($b_1$))

By exactly following the same hydrogenolysis procedure as that described in Example 5, from 34.3 g of the compound of Example 4(a), 24.5 g of crude title compound (HPLC, about 55%) are obtained.

Example 6: Removal of the Tert-Butoxycarbonyl Protecting Groups from the Compound of Example 5 (step ($b_1$))

The crude product of Example 5 (3.2 g) is dissolved in 50 ml of trifluoroacetic acid. The resulting solution is stirred at room temperature for 1.5 hours, then the solvent is evaporated at room temperature under reduced pressure. The oily residue is slurried with diethyl ether yielding a solid which is collected and washed with diethyl ether (50 ml). This procedure yields 2.7 g of crude product containing about 40% (HPLC) of the title compound which is purified by reverse-phase column chromatography as described hereinafter.

The above crude product is dissolved in 50 ml of a mixture acetonitrile:water 1:1 (v/v) and the resulting solution is adjusted at pH 3.5 with 1N sodium hydroxyde, then it is diluted with 250 ml of water and loaded on a column of 250 g of silanized silica-gel (0.06–0.2 mm Merck) in water. The column is developed with a linear gradient from 15% to 50% (v/v) of acetonitrile in water in 20 hours at a flow-rate of about 100 ml/hour, while collecting 10 ml fractions. Those fractions containing (HPLC) pure title compound are pooled, and the solvent is evaporated (in the presence of enough n-butanol to avoid foaming) at 40° C. under reduced pressure, yielding 400 mg (about 25%) of pure title compound. (HPLC, method a: $t_R$=9.0 minutes).

Example 6(a): Removal of the Tert-Butoxycarbonyl Protecting Groups from the Compound of Example 5(a) (Step ($b_1$))

The crude product of example 5(a)(24.5 g) is dissolved in 300 ml of trifluoroacetic acid. The resulting solution is stirred at room temperature for 30 minutes, then the solvent is evaporated at room temperature under reduced pressure. The oily residue is slurried with diethyl ether, yielding a solid which is collected and washed with diethyl ether (200 ml). This procedure yields 21 g of crude (HPLC, about 55%) title compound which is then purified by reversed-phase column chromatography on silanized silica-gel according to the same procedure as that described in Example 6, thus giving 9.7 g (about 60%) of pure title compound. (HPLC, method a: $t_R$=11.3 minutes)

Example 7: Edman Degradation of the Product of
Example 6 (Step (c₁); Formula (Ic): R+
R₀=Amino, R₁=R₂λR₅=hydrogen,
R₃=R₄λChloro, R₆=Hydroxy, Y=Carboxy)

To a stirred solution of 1 g (0.82 mmol) of the product of Example 6 in 20 ml of a mixture pyridine:water 1:1 (v/v), a solution of 145 mg (1.98 mmol) of methylisothiocyanate in 2.5 ml of the same solvent mixture is added dropwise at room temperature. The reaction mixture is stirred at room temperature for 16 hours, then it is poured into 50 ml of water. The cloudy aqueous solution is extracted with 100 ml of diethyl ether (the organic layer is discarded), then it is adjusted at pH 3 with 1N hydrochloric acid and extracted with 100 ml of n-butanol. The organic layer is washed with water (4×100 ml) and then it is concentrated at 40° C. under reduced pressure to a small volume. On adding 200 ml of diethyl ether, a solid separates which is collected by filtration (1.1 g) and re-dissolved in 25 ml of trifluoroacetic acid. The resulting solution is stirred at 50° C. for 10 minutes, afterwards the solvent is evaporated. The oily residue is slurried with 50 ml of diethyl ether giving a solid which is collected by filtration, washed with 50 ml of diethyl ether and dried at room temperature in vacuo overnight. Yield 0.96 g of crude (about 60%, HPLC titre) title compound.

This product is purified by reverse-phase column chromatography as above described for the final purification of the compound of example 6, yielding 240 mg of pure title compound, as the di-trifluoroacetate.

The internal salt (140 mg) can be obtained by dissolving 200 mg of the di-trifluoroacetate in 5 ml of water, adjusting the solution at pH 6.5 with 1N NaOH and filtering the solid which separates. (HPLC, method a: $t_R$=6.8 minutes)

Example 7(a): Edman Degradation of the Product
of Example 6(a) (Step (c₁)); Formula (Ic): R=
R₀=Amino, R₁=R₂=R₅=Hydrogen,
R₃=R₄=Chloro, R₆=Hydroxy, Y=Carbomethoxy)

A solution of 6.5 g (about 5 mmol) of the product of Example 6(a) and 1.25 ml (about 10 mmol) of phenylisothiocyanate in 100 ml of a pyridine:water 1:1 (v/v) mixture is stirred at room temperature for 3 hours. Afterwards, the reaction mixture is poured into 200 ml of water and the resulting cloudy solution is adjusted to pH 3 with 1N HCl, then is is extracted with ethyl acetate (2×200 ml). The organic layer is discarded and the aqueous phase is extracted again with 200 ml of 1-butanol. The organic layer is separated, washed with water (2×200 ml), then it is concentrated at 40° C. under reduced pressure, to a small volume (about 30 ml). On adding diethyl ether (about 100 ml) a solid precipitate is obtained which is collected, washed with diethyl ether and dried at room temperature in vacuo overnight, yielding 6.7 g of the intermediate diphenylisothiourea which is used without any further purification in the successive step. The above product is dissolved in 150 ml of dry trifluoroacetic acid and the resulting solution is stirred at 50° C. for 10 minutes, afterwards the solvent is evaporated. The oily residue is purified by reversed-phase column chromatography as above described for the final purification of the compound of Example 6a, yielding 1.35 g of pure title compound, as the di-trifluoroacetate (HPLC, method a: $t_R$=10.3 minutes)

Example 8: Edman Degradation of the Compound
of Example 1 (Step (b₂))

To a stirred solution of 13 g (10.83 mmol) of the compound of Example 1 in 260 ml of a mixture pyridine:water 1:1 (v/v), a solution of 1.9 g of methylisothiocyanate in 40 ml of the same solvent mixture is added dropwise at room temperature. The reaction mixture is stirred at room temperature for 22 hours. Afterwards, it is concentrated at 35° C. under reduced pressure to dryness. The oily residue is re-dissolved in 300 ml of toluene and the solvent is evaporated, yielding a solid (18 g) which is slurried with diethyl ether and suspended in 400 ml of water. The resulting suspension is adjusted at pH 3 with 1N HCl and extracted with n-butanol (2×200 ml). The organic layer is washed with water (400 ml) and then it is concentrated at 40° C. under reduced pressure to a final volume of about 50 ml. On adding 450 ml of diethyl ether, a solid separates which is collected by filtration and washed with 150 ml of water, then with 500 ml of diethyl ether. Yield 13.2 g (about 95%; HPLC titre) of bis-(methylthiocarbamyl) intermediate. (HPLC, method a: $t_R$=15.1 minutes)

This product is dissolved in 100 ml of trifluoroacetic acid. The resulting solution is stirred at 50° C. for 10 minutes (in the meantime a red solution forms), and then the solvent is evaporated at room temperature under reduced pressure. The oily residue is slurried with diethyl ether (350 ml) and the solid which forms is collected by filtration, washed with 250 ml of diethyl ether and then dried at room temperature in vacuo overnight, obtaining 12 g of crude (74%; HPLC titre) title compound which is used without any further purification for the next step. An analytical pure sample (250 mg) is prepared by reverse-phase column chromatography under the same conditions as those previously described in Example 6. (HPLC, method a: $t_R$=11.3 minutes)

Example 9: Protection of the Amino Functions of
the Compound of Example 8 with Tert-
Butoxycarbonyl Groups (Step (c₂))

To a stirred solution of 11.5 g of the crude product of Example 8 in 250 ml of a mixture water:dioxane 1:1 (v/v), 12 g of sodium bicarbonate is added. Then, the resulting suspension is cooled to 0° C. and a solution of 6 g of di-tert-butyl-dicarbonate in 50 ml of dioxane is added dropwise while cooling at 0°–5° C. The reaction mixture is stirred at room temperature for 5 hours; afterwards it is adjusted at pH 4 with 1N HCl and extracted with 250 ml of ethyl acetate. The organic layer is separated, washed with water (2×200 ml) and then it is dried over sodium sulfate. After concentration at 30° C. under reduced pressure to a small volume (about 30 ml), diethyl ether (300 ml) is added and the precipitated solid is collected to give 8.6 g of crude (85%; HPLC titre) title compound which is purified by reverse-phase chromatography under the same conditions as those described in Example 6, but eluting with a linear gradient from 20% to 70% of acetonitrile in water, to yield 6.7 g of pure title compound. (HPLC, method b: $t_R$=12.2 minutes)

Example 10: Protection of the Phenolic Hydroxy
Groups of the Compound of Example 9 with
Carbobenzyloxy Groups (Step (c₂))

To a stirred suspension of 6 g (5.5 mmol) of the compound of Example 9 in 500 ml of anhydrous acetone, 120 ml of 2,2-dimethoxypropane and 0.27 g (1.4 mmol) of p-toluenesulfonic acid are added. After stirring for 90 minutes, a solution of 0.24 g of sodium bicarbonate in 4 ml of water is added. The resulting solution (pH 6.3) is concentrated at 35° C. under reduced pressure to dryness and the solid residue is collected, obtaining 6.4 g of the oxazolidino intermediate which is then carbobenzoxylated on the phenolic hydroxy groups according to the alternative methods A and B described herein below. (HPLC, method b: $t_R$=17.9 minutes)

Method A:

To a stirred solution of 0.39 g (0.34 mmol) of the above oxazolidine intermediate in 12 ml of dry dimethylsulfoxide, 0.57 g (4.13 mmol) of potassium carbonate is added. After 30 minutes, 0.58 ml (4.13 mmol) of triethylamine and a solution of 0.48 ml (3.4 mmol) of benzylchloroformate in 2 ml of tetrahydrofuran are added while cooling to 15° C. After stirring at room temperature for 24 hours, an additional amount of 0.57 g of potassium carbonate followed by 0.48 ml of benzylchloroformate are added at 15° C. After 30 minutes at room temperature under vigorous stirring, the reaction mixture is poured in a solution of 5 ml of glacial acetic acid in 95 ml of water. The resulting solution is extracted with ethyl acetate (2×200 ml). The organic layer is separated, washed with water (2×150 ml), and then dried over sodium sulfate. The solvent is evaporated at 40° C. under reduced pressure and the oily residue is slurried successively with petroleum ether and diethyl ether to give 0.42 g of a mixture of at least three main components (HPLC), corresponding to the title compound with different degrees of protection at the phenolic groups.

This product, without any further purification, is suitable for the successive reaction step. (HPLC, method c: $t_R$=19.1, 30.6, 33.4 minutes)

Method B:

To a stirred solution of 2.1 g (1.86 mmol) of the above oxazolidine intermediate in 70 ml of dry dimethylsulfoxide, 3.63 g (11.2 mmol) of cesium carbonate is added. After stirring at room temperature for 90 minutes, 2.8 ml (20 mmol) of benzyl chloroformate is added dropwise at 20°–25° C. The reaction mixture is stirred at room temperature for 5 minutes and then it is poured into a solution of 5 ml of glacial acetic acid in 250 ml of water. The resulting solution is worked up as described above under Method A, yielding 3 g of a mixture of two main products (HPLC) corresponding to the two more lipophilic components of the mixture obtained by Method A.

This product is more suitable for the successive reaction step. (HPLC, method c: $t_R$=30.6 (15%), 33.4 (85%) minutes)

To a stirred suspension of the product (3 g) obtained according to Method B above in 150 ml of acetonitrile, 15 ml of 1N hydrochloric acid is added and the resulting solution is stirred at room temperature for 90 minutes. Afterwards, a stirred mixture of 350 ml of water and 500 ml of ethyl acetate is added. The organic layer is separated and washed with a 1M solution of sodium bicarbonate in water until the pH of the aqueous washings is neutral. After an additional washing with 300 ml of water, the organic layer is dried over sodium sulfate and concentrated to a small volume (about 30 ml) at room temperature under reduced pressure. On adding diethyl ether (270 ml), a solid separates which is collected by filtration, washed with diethyl ether (100 ml), and then dried at room temperature in vacuo to yield 2.45 g of the title compound as a mixture showing a components ratio (HPLC) corresponding to the one of the respective oxazolidine precursor (but with relative retention times about 6 minutes lower). This product is used without any further purification for the successive oxidation reaction. (HPLC, method c: $t_R$=23.7, 27.1 minutes)

Example 11: Oxidation of the Hydroxymethyl Group of the Product of the Example 10 to Carboxy (Step ($c_2$); Formula (Ic)): R=$R_0$=Tert-Butoxycarbonylamino, $R_1$=$R_2$=$R_5$=Hydrogen, $R_3$=$R_4$=Chloro, $R_6$=Hydroxy, Y=Carboxy, wherein the Phenolic Hydroxy Groups are Protected by Carbobenzyloxy Rests)

The above product (2.45 g) is oxidized with the Jones reagent under the same conditions as those described in Example 4 obtaining 2.3 g of the title compound as a mixture of two main components in a ratio 85:15 (HPLC).

(HPLC, method c: $t_R$=14.5 (15%), 18.7 (85%) minutes)

Example 12: Removal of the Carbobenzyloxy Protecting Groups from the Compound of Example 11 (Step ($c_2$)); Formula (Ic): R=$R_0$=Tert-Butoxycarbonylamino, $R_1$=$R_2$=$R_5$=Hydrogen, $R_3$=$R_4$=chloro, $R_6$=Hydroxy, Y=Carboxy)

The product of Example 11 (2.3 g) is hydrogenated under the same conditions as those described in Example 5 obtaining 1.3 g of the title compound. (HPLC, method b: $t_R$=7.9 minutes)

Example 13: Removal of the Tert-Butoxycarbonyl Protecting Groups from the Compound of Example 12 (Step ($c_2$)); Formula (Ic): R=$R_0$=Amino, $R_1$=$R_2$=$R_5$=Hydrogen, $R_3$=$R_4$=Chloro, $R_6$=Hydroxy, Y=Carboxy)

A solution of the above product (1.3 g) in 30 ml of trifluoroacetic acid is stirred at room temperature for 2 hours, then the solvent is evaporated at 30° C. under reduced pressure. The oily residue is slurried with diethyl ether (100 ml) and the solid which forms is collected by filtration. Purification by reverse-phase chromatography under the same conditions of Example 6 yields 1.05 g of pure title compound, as the di-trifluoroacetate. (HPLC, method a: $t_R$=6.8 minutes)

Analytical procedures (Examples 1–13)

1) HPLC Methods

Reactions, column eluates and final products are checked by HPLC analyses, which are performed on a column Hibar (250×4 mm, Merck) pre-packed with Li-Chrosorb RP-8 (10 um), using a Varian Model 5500 Liquid Chromatographic pump equipped with a 20 µl loop injector Rheodyne Model 7125 UV variable detector. Chromatograms are recorded at 254 nm. Elutions are carried out at a flow-rate of 2 ml/minute by mixing Eluent A, 0.2% aqueous ammonium formate, with Eluent B, acetonitrile, according to linear step gradients programmed as follows:

| Method a. | | | | | | |
|---|---|---|---|---|---|---|
| Time (minutes): | 0 | 10 | 20 | 30 | 35 | 45 |
| % of B in A: | 5 | 23 | 26 | 35 | 75 | 5 |
| Method b. | | | | | | |
| Time (minutes): | 0 | 30 | 35 | 40 | 45 | |
| % of B in A: | 20 | 60 | 75 | 75 | 20 | |
| Method c. | | | | | | |
| Time (minutes): | 0 | 30 | 35 | 40 | 45 | |
| % of B in A: | 40 | 75 | 85 | 85 | 40 | |

2) Acid-base titrations

Acid-base titrations are carried out under the following conditions: the sample is dissolved in a mixture methyl cellosolve:$H_2O$, then an excess of 0.01M HCl in the same solvent mixture is added and the resulting solution is titrated with 0.01N NaOH.

Table II shows the equivalent weight of some tetrapeptide compounds and intermediates

3) $^1$H-NMR

The 1H NMR spectra are recorded with a 24 mg solution of the proper product in 0.5 ml of DMSO-$d_6$ at 303° K. on a Bruker AM 500 NMR-spectrometer equipped with an Aspect 3000 computer, using $(CH_3)_4Si$ (δ 0.00 ppm) as internal reference. In particular, in Table II are reported only the significative δ values concerning the characterizing portions of some end compounds and intermediates.

For $^{13}C$ spectra the spectrometer frequency was 125.17 MHz.

The newly introduced carbonyl functions were determined in a $^1H$-detected heteronuclear multiple-bond correlation spectroscopy (M. Bax and D. Marier, J. Magn. Reson. 78, 186, 1988).

Table III shows $^1H$-NMR and $^{13}C$ data of some tetrapeptide compounds and intermediates. 4) FAB-MS FAB-MS positive ion spectra are obtained on a Kratos MS-50 double focusing mass spectrometer of 3000 dalton mass range, using 8 kV accelerating voltage. The instrument is operating under computer control. To obtain high quality data, a DS-90 data system in "raw data" acquisition is used. For FAB, a saddle field atom gun is used with Xe gas ($2\times10^{-5}$ tort pressure indicated on the source ion gauge) at 6 kV voltage and 1 mA current. The samples are dissolved in a mixture methanol:H2O 1:1 containing 0.2N HCl or, alternatively, in dimethylformamide (DMF). Then, 1 microliter of this solution is mixed with 1 microliter of thioglycerol matrix eventually containing a 1N acetic acid on the target. Table II shows the molecular weight of some tetrapeptide compounds and intermediates.

TABLE II

Molecular weight and equivalent weight

| Compound (Example) | Formula | M.W | FAB-MS [M + H]$^+$ | Potentiometric titration E.W. |
|---|---|---|---|---|
| Ex. 6 | $C_{58}H_{47}Cl_2N_7O_{19}$ | 1217 | 1216.3 | 543 (x2) |
| Ex. 8 | $C_{42}H_{37}Cl_2N_5O_{13}$ | 889 | 890.2 912.2 [M + Na]$^+$ | n.d. |
| Ex. 7 (13) | $C_{42}H_{35}Cl_2N_5O_{14}$ | 905 | 904.2 | n.d. |
| Ex. 5 | $C_{64}H_{63}Cl_2N_7O_{23}$ | 1417 | 1416.2 | n.d. |
| Ex. 9 | $C_{52}H_{53}Cl_2N_5O_{17}$ | 1089 | 1090.1 1112.1 [M + Na]$^+$ | n.d. | n.d.: not determined

TABLE III $^1H$-NMR and $^{13}C$-NMR data in MDSO-d$_6$; (CH$_3$)$_4$Si internal standard, δ0.00 ppm

| Compound Example | δppp |
|---|---|
| 5 | $^1H$: 1.32 and 1.38 (tert.butoxycarbonyl group) |
| 6 | $^1H$: 4.08–5.70 (peptidic CH's); 6.28–9.75 (aromatic protons and peptidic NH's) $^{13}C$: 171.3 (additional —COOH) |
| 7 and 13 | $^1H$: 3.75–5.45 (peptidic CH's); 6.28–9.12 (aromatic protons and peptidic NE's) $^{13}C$: 170.8 ppp (additional —COOH) |
| 8 | $^1H$: 3.45–5.15 (peptidic CH's); 3.57, 3.45 (—CH$_2$OH); 5.5–9.11 (aromatic protons and peptidic NH's) |
| 9 | $^1H$: 1.27 and 1.33 (tert.butoxycarbonyl group) |
| 12 | $^1H$: 1.28 and 1.32 (tert.butoxycarbonyl group) |

The analytical methods and procedures utilized for the characterization of the compounds prepared according to the following examples 14–17 are described in a separate paragraph following this series of examples.

Example 14—Preparation of N$^B$-Benzyloxycarbonyl-Agluco-Teicoplanin Tetrapeptide Methyl Ester [N$^B$-CBZ-ATTP Methyl Ester; Reaction Scheme 3, Formula (I')]

i) Preparation of N$^A$-tert-butoxycarbonyl-aglucoteicoplanin tetrapeptide methyl ester (N$^A$-t-BOC-ATTP methyl ester)

A stirred solution of 3 g (about 3 mmol) of ATTP methyl ester (the synthesis of this compound is described in Example 7a) in 100 ml of dioxane:water 1:1 mixture is adjusted at pH 7 by adding solid NaHCO$_3$. Then, a solution of 0.65 g (about 3 mmol) of di-tert-butyldicarbonate in 20 ml of dioxane is added dropwise while cooling at 0° C. The reaction mixture is stirred at 0° C. for 18 hours, and then is poured into 400 ml of a mixture water:ethyl acetate 1:1. After adjusting at pH 3 with 1N HCl:

a) The organic layer is separated, washed with water (3×100 ml), dried over Na$_2$SO$_4$, and then it is concentrated, at 30° C. under reduced pressure, to a small volume (about 25 ml). On adding diethyl ether (108 ml), the precipitated solid is collected, yielding 1.4 g of side-product N$^A$,N$^B$-di-(t-BOC)-ATTP methyl ester (HPLC: Method A$^1$, t$_R$ 25.2 minutes);

b) The aqueous phase is extracted with an equal volume of butanol and the butanolic layer is concentrated at 40° C. under reduced pressure to a small volume (about 30 ml). On adding diethyl ether (100 ml), the precipitated solid is collected to give 1.5 g of N$^A$-t-BOC-ATTP methyl ester (TABLE IV, compound a; HPLC: Method A$^1$, 16.4 minutes).

The above di-protected side-product N$^A$, N$^B$-di-(t-BOC)-ATTP methyl ester (1.4 g) is treated with trifluoroacetic acid (50 ml) at room temperature (10 minutes) to regenerate ATTP methyl ester (1.15 g) which is then transformed into 0.7 g of N$^A$-t-BOC-ATTP methyl ester and 0.5 g of the above side product under the same above conditions. By repeating this process three times, the overall conversion yield of ATTP methyl ester to N$^A$-t-BOC-ATTP methyl ester is about 80%.

ii) Preparation of N$^A$-tert-butoxycarbonyl-N$^B$-benzyloxycarbonyl aglucoteicoplanin tetrapeptide methyl ester (N$^A$-t-BOC-NB-CBZ-ATTP methyl ester).

To a stirred solution of 2.35 g (about 2.3 mmol) of N$^A$-t-BOC-ATTP methyl ester in 100 ml of a dioxane:water 1:1 mixture, which is adjusted at pH 7 with solid NaHCO$_3$, a solution of 0.32 ml (about 2.3 mmol) of benzyl chloroformate in 10 ml of dioxane is added dropwise at room temperature in 10 minutes. The reaction mixture is stirred at room temperature for 20 minutes and then it is poured into 150 ml of water. The resulting cloudy solution is adjusted at pH 3 with 1N HCl and extracted with 200 ml of ethyl acetate. The organic layer is separated, dried over Na$_2$SO$_4$, and then it is concentrated, at 30° C. under reduced pressure, to a small volume (about 20 ml). On adding diethyl ether (100 ml), the precipitated solid is collected, yielding 2.4 g of N$^A$-t-BOC-N$^B$-CBZ-ATTP methyl ether (TABLE IV, compound b; HPLC: Method B$^1$, t$_R$ 11.8 minutes).

iii) Preparation of N$^B$-CBZ-ATTP methyl ester.

A solution of N$^A$-t-BOC-N$^B$-CBZ-ATTP methyl ester (2.4 g) in 108 ml of dry trifluoroacetic acid is stirred at room temperature for 10 minutes, and then the solvent is evaporated at 35° C. under reduced pressure. The oily residue is dissolved in 300 ml of a mixture water:ethyl acetate 1:1. The organic layer is separated, washed twice with water (2×158 ml), dried over Na2SO$_4$, and then it is concentrated, at 40° C. under reduced pressure, to a small volume (about 15 ml). On adding diethyl ether (100 ml) the solid precipitate is collected to give 2 g of N$^B$-CBZ-ATTP methyl ester as trifluoroacetate (TABLE IV, compound c; HPLC: Method B, t$_R$ 8.3 minutes).

Example 15 Preparation of N$^B$-Benzyloxycarbonyl-(L-Phenylalanyl)$^3$-Aglucoteicoplanin Pentapeptide Methyl Ester [N$^B$-CBZ-(L-Phenylalanyl)3-ATPP Methyl Ester; Reaction Scheme 3, formula (VII)]

i) Preparation of N$^B$-benzyloxycarbonyl-(N-tert-butoxycarbonyl-L-phenylalanyl)$^3$-aglucoteicoplanin pentapeptide methyl ester [(N$^B$-CBZ-(N-t-BOC-L-phenylalanyl)$^3$-ATPP methyl ester].

To a stirred solution of 1 g (about 0.9 mmol) of N$^B$-CBZ-ATTP methyl ester trifluoroacetate in 20 ml of dimethylformamide, 0.13 ml (about 0.9 mmol) of triethylamine is added at room temperature followed by 0.34 g (about 0.9 mmol) of the ester of N-t-BOC-L-phenylalanine with N-hydroxysuccinimide (Sigma Chemical Co., St. Loius, USA). After 3 hour stirring at room temperature, 100 ml of water is added and the resulting solution is adjusted at pH 3 with 1N HCl. Extraction with n-butanol (100 ml) and evaporation of the solvent yield 0.9 g of N$^B$-CBZ-(N-t-BOC-L-phenylalanyl)$^3$-ATPP methyl ester (TABLE IV, compound d; HPLC: Method B$^1$, t$_R$ 14.9 minutes);

ii) Preparation of [N$^B$-CBZ-(L-phenylalanyl)$^3$-ATPP methyl ester].

A solution of N$^B$-CBZ-(N-t-BOC-L-phenylalanyl)$^3$-ATPP methyl ester (220 mg) in 10 ml of dry trifluoroacetic acid is stirred at room temperature for 15 minutes and then the solvent is evaporated at 30° C. under reduced pressure. The oily residue is slurried with diethyl ether to give 200 mg N$^B$-CBZ-(L-phenylalanyl)$^3$-ATPP methyl ester as trifluoroacetate (TABLE IV, compound e; HPLC: Method B$^1$ t$_R$ 10.2 minutes).

Example 16 Preparation of (L-phenylalanyl)$^3$-agluco-teicoplanin hexapeptide methyl ester [(L-phenylalanyl)$^3$-ATHP methyl ester; Reaction Scheme 3, formula (VIII)]

i) Preparation of N$^B$-benzyloxycarbonyl-(L-phenylalanyl)$^3$-aglucoteicoplanin hexapeptide methyl ester [N$^B$-CBZ-(L-phenylalanyl)$^3$-ATHP methyl ester].

To a stirred solution of 0.4 g (about 0.34 mmol) of N$^B$-CBZ-(L-phenylalanyl)$^3$-ATPP methyl ester in 40 ml of a dimethylformamide:dichloromethane 1:1 mixture, 0.047 g (about 0.34 mmol) of N-hydroxybenzotriazole hydrate and 0.038 ml (about 0.34 mmol) of N-methyl-morpholine are added at room temperature followed by 0.085 g (about 0.4 mmol) of dicyclohexylcarbodiimide. The reaction mixture is stirred at room temperature overnight and then the methylene chloride solvent is evaporated at 30° C. under reduced pressure. Afterwards, 200 ml of a water:ethyl acetate 1:1 mixture is added dropwise under stirring. The resulting mixture is adjusted at pH 3 with 1N HCl and the insoluble matter is filtered off. Then, the organic layer is separated and the solvent is evaporated at 35° C. under reduced pressure. The solid residue is dissolved in 50 ml of a mixture water:acetonitrile:n-butanol 1:1:2 and 5 g of silanized silica-gel 60 (0.06–0.2 mm(Merck) is added under stirring. After 30 minutes, the solvents are evaporated at 45° C. under reduced pressure and the solid residue is loaded on a column of 35 g of the same silanized silica-gel in water. The column is developed with a linear gradient from 10 to 70% of acetonitrile in water in 15 hours at the flow-rate of 100 ml/hour, while collecting 10 ml-fractions which are checked by HPLC. Those fractions containing pure title compound are pooled and an equal volume of n-butanol is added. The resulting solution is concentrated, at 40° C. under reduced pressure, to a small volume (about 10 ml), and then diethyl ether (100 ml is added). The precipitated solid is collected and added to 20 ml of dimethylsulfoxide. The resulting suspension is filtered and the clear filtrate is lyophilized, yielding 0.11 g of pure N$^B$-CBZ-(L-phenylalanyl)$^3$-ATHP methyl ester (Table IV, compound f; HPLC: Method B$^1$, t$_R$ 22.6 minutes).

The $^1$H-NMR data (delta, ppm) of protons are reported hereinbelow (the protons identification is made in accordance with J. C. J. Barna, et al. J. Am. Chem. Soc. 1984, 106, 4895–4902):

8.69(w$_5$); 8.65(w$_7$); 8.38(w$_4$); 7.87(6b); 7.70(w$_3$); 7.45(w$_2$); 6.60(w$_6$); 6.44(7d); 6.23(4b); 6.10(7f); 5.82(x$_4$); 5.40(4f); 5.13(z$_6$); 4.97(CBZ—CH$_2$); 4.60(x$_2$); 4.60(x$_5$); 4.54(x$_7$); 4.25(x$_3$); 4.24(x$_6$); 3.71(COO—CH$_3$); 2.85, 2.72(z$_2$,z$_3$,); 2.43, 2.25(Phe—CH$_2$).

ii) Preparation of (L-phenylalanyl)$^3$-ATHP methyl ester

A solution of 1.8 g (about 1.5 mmol) of N$^B$-CBZ-(L-phenylalanyl)$^3$-ATHP methyl ester in 120 ml of a mixture methanol:1N HCl:dimethylformamide 6:2:1 is hydrogenated (1 atm, 25° C.) in the presence of 1.5 g of 5% Pd/C. The catalyst is filtered off and methanol is evaporated at 35° C. under reduced pressure; then, 100 ml of water is added and the resulting solution is extracted with 150 ml of ethyl acetate. The organic layer is discarded and the resulting aqueous suspension is extracted with 130 ml of n-butanol. The butanolic phase is separated and concentrated at 30° C. under reduced pressure to a volume of about 20 ml. After addition of 150 ml of diethyl ether the precipitated solid is collected yielding 0.65 g of (L-phenylalanyl)$^3$-ATHP methyl ester as the hydrochloride (HPLC: Method B, t$_R$ 17.5 minutes, titer about 75%) which is used for the next step without any further purification.

Example 17 Preparation of (L-phenylalanyl)$^3$-(D-lysyl)$^{15}$-aglucoteicoplanin dalbaheptide methyl ester; [(L-phenylalanyl)$^2$-(D-lysyl)$^{15}$-ATDH methyl ester; Reaction Scheme 3, formula (VIc)]

i) Preparation of (L-phenylalanyl)$^3$-[N$^{α}$,N$^{ε}$-di-(tert-butoxycarbonyl)-D-lysyl]$^{15}$-aglucoteicoplanin dalbaheptide methyl ester [(L-phenylalanyl)$^3$-[N$^{α}$,N$^{ε}$-di-(t-BOC)-D-lysyl]$^{15}$-ATDH methyl ester)].

To a stirred solution of 0.29 g of crude (L-phenylalanyl)$^3$-ATHP methyl ester hydrochloride 3 ml of dimethylformamide, 0.07 ml triethylamine and 0.19 g of the ester of N$^{α}$,N$^{ε}$-di-(t-BOC)-D-lysine with N-hydroxy succinimide (prepared according to the method described by M. J. Marquisee and J. C. Kower, J. Med. Chem., 21: 1188–1194, 1978) are added at room temperature. After 1 day reaction, 50 ml of water is added and the resulting suspension is adjusted at pH 3 with 1N HCl; then, it is extracted with 50 ml of n-butanol. The organic layer is separated and washed with 25 ml of water; then, it is concentrated at 45° C. under reduced pressure to a small volume (about 3 ml). After addition of diethyl ether (30 ml), the precipitated solid is collected yielding 0.27 g of (L-phenylalanyl)$^3$-[N$^{α}$,N$^{ε}$-di-(t-BOC)-D-lysyl]$^{15}$-ATDH methyl ester, (HPLC: Method B$^1$, t$_R$ 22.5 minutes, titre about 45%). The compound is used without any purification for the final step.

ii) Preparation of (L-phenylalanyl)$^3$-(D-lysyl)$^{15}$-ATDH methyl ester.

The crude (L-phenylalanyl)$^3$-[N$^{α}$,N$^{ε}$-di-(t-BOC)-D-lysyl]$^{15}$-ATDH methyl ester (0.27 g) is dissolved at 10° C. in 5 ml of dry trifluoroacetic acid. After 10 minutes, the solvent is evaporated at 15° C. under reduced pressure. The oily residue is dissolved in 30 ml of a mixture water:methanol: 1:1 and the resulting solution is adjusted at pH 3.5 with 1N NaOH; then, it is loaded on a column of 50 g of silanized silica-gel. Column chromatography is performed as previously described for the purification of N$^B$-CBZ-(L-phenylalanyl)$^3$-ATHP methyl ester in Example 163, obtaining 0.05 g of pure title compound as the trifluoroacetate. The product is then dissolved in 1 ml of water and the pH adjusted at 8.5 with 1N NaOH. The solid precipitate is collected and washed with water (2×2 ml), obtaining title compound (0.045 g) as the free base (TABLE IV, compound g; HPLC: Method B$^1$, t$_R$ 18.3 minutes).

The $^1$H-NMR data (delta ppm) of protons are reported hereinbelow (trifluoroacetate): 1.28, 1.45, 1.68, 2.93(Lys-CH$_2$S); 3.71(COO—CH$_3$); 4.14–5.34[peptidic alpha—CH's (x$_1$ to x$_7$; 4.14 ppm attributable to x$_1$, and 5.34 ppm to X$_4$]; 6.64–8.59 (aromatic protons and peptidic NH's).

ANALYTICAL PROCEDURES (Examples 14–17)

1) HPLC Methods

Reactions, column eluates and final products are checked by HPLC analyses, which are performed on a column LiChroCART (125×4 mm, Merck) pre-packed with LiChrospher RP (5 µm), using a Varian Model 5500 Liquid Chromatographic pump equipped with a 20 µl loop injector Rheodyne Model 7125 and a UV variable detector. Chromatograms are recorded at 254 mm. Elutions are carried out at a flow-rate of 1.5 ml/minutes by mixing Eluent (a): 0.2% aqueous ammonium formate, with Eluent (b): acetonitrile, according to linear step gradients programmed as follows:

| Method A$^1$. | | | | | | |
|---|---|---|---|---|---|---|
| Time (minutes): | 0 | 10 | 20 | 30 | 35 | 45 |
| % of (b) in (a): | 5 | 23 | 26 | 35 | 75 | 5 |
| Method B$^1$: | | | | | | |
| Time (minutes): | 0 | 30 | 35 | 40 | 45 | |
| % of (b) in (a): | 20 | 60 | 75 | 75 | 20 | |

2) Acid-base Titrations

Acid-base titrations are carried out under the following conditions: the sample is dissolved in a mixture methylcellosolve:water 4:1, then an excess of 0.01M HCl in the same solvent mixture is added and the resulting solution in titrated with 0.01N NaOH.

3) $^1$H NMR

The $^1$H NMR spectra are recorded in DMSO-d$_6$ solution at 303° K. on a Bruker AM 500 NMR-spectrometer equipped with an Aspect 3000 computer, using (CH$_3$)$_4$Si (delta 0.00 ppm) as internal reference.

4) FAB-MS

FAB-MS positive ion spectra are obtained on a Kratos MS-50 double focusing mass spectrometer of 3000 dalton mass range, using 8 kV accelerating voltage. The instrument operates under computer control. To obtain high quality data, a DS-90 data-system in "raw data" acquisition is used. For FAB, a saddle field atom gun is used with Xe gas (2×10$^{-5}$ tort pressure indicated on the source ion gauge) at 6 kV voltage and 1 mA current. The samples are dissolved in a mixture methanol:water 1:1 containing 0.2N HCl or, alternatively in dimethylformamide. Then, 1 microliter of this solution is mixed with 1 microliter of thioglycerol matrix, optionally containing 1N acetic acid on the target.

TABLE IV

Analytical Data

| Compound | Formula | M.W. | FAB-MS [M + H]$^+$ | Acid-base Titration E.W. |
|---|---|---|---|---|
| a | C$_{48}$H$_{45}$N$_5$O$_{16}$Cl$_2$ | 1018.8 | 1020 | 535 |
| b | C$_{56}$H$_{51}$N$_5$O$_{18}$Cl$_2$ | 1152.9 | 1154 | 1200 |
| c | C$_{51}$H$_{43}$N$_5$O$_{16}$Cl$_2$ | 1052.8 | 1054 | 573 |
| d | C$_{65}$H$_{60}$N$_6$O$_{19}$Cl$_2$ | 1300.1 | 1301 | 1285 |
| e | C$_{60}$H$_{52}$N$_6$O$_{17}$Cl$_2$ | 1200.0 | 1201 | 587 |
| f | C$_{50}$H$_{50}$N$_6$O$_{16}$Cl$_2$ | 1182.0 | 1183 | — |
| g | C$_{58}$H$_{56}$N$_8$O$_{15}$Cl$_2$ | 1176.0 | 1177 | 599 |

REFERENCES

1. U.S. Pat. No. 4,456,593
2. Rajananda, V., Norris A. F., and Williams D. H.: Characterization of beta-hydroxytyrosine unit in ristocetin A. J. Chem. Soc. Perkin Trans. I, 1979: 29–31.
3. Bognar, R. Sztaricskai, F., Hunk, M. E. and James, J. Structure and stereochemistry of ristosamine. J. Org. Chem. 1974,39: 2971–2974.
4. Williams, D. H., Rajananda, V., Bojesen, G. and Williamson, M. P. Structure of the antibiotic ristocetin A. J.C.S. Chem. Comm. 1979: 906–908.
5. Malabarba, A., Strazzolini, P., DePaoli, A., Landi, M., Berti, M. and Cavalleri, B. Teicoplanin, antibiotics from Actinoplanes teichomyceticus nov. sp. VI. Chemical degradation: physico-chemical and biological properties of acid hydrolysis products. J Antiblot 1984; 37: 988–999.
6. European Patent Appl. Publ. No. 301 247
7. European Patent Appl. Publ. No. 290 922
8. European Patent Appl. Publ. No. 376 041
9. European Patent Appl. Publ. No. 316 712
10. Marshal F. J., Structure studies on vancomycin. J. Med. Chem. 1965, 8:18–22.
11. European Patent Appl. Publ. No. 159 863
12. European Patent Appl. Publ. No. 240 609
13. McGahren, W. J., Leese, R. A., Barbatschi, F., Morton, G. O., Kuck, N. A. and Ellestad, G. A. Components and degradation compounds of the avoparcin complex. J Antibiot 1983; 36: 1671–1682.
14. McGahren, W. J., Martin, J. H., Morton, G. O., Hargreaves, R. T., Leese, R. A., Lovell, F. M., Ellestad, G. A., O'Brien, E. and Holker, J. S. E. Structure of avoparcin components. J Am Chem Soc 1980; 102:1671–1684.
15. European Patent Appl. Publ. No. 255 299.
16. Arjuna Rao, V., Ravishankar, D., Sadhukhan, A. K., Ahmed, S. M., Goel, A. K., Prabhu, N. S., Verma, A. K., Venkateswarlu, A., Allaudeen, H. S., Hedde, R. H. and Nisbet, L. J. Synmonicins: a novel antibiotic complex produced by Synnemomyces mamnoorii gen. et. sp. nov. I. Taxonomy of the producing organism, fermentation and biological properties, 26th Intersci Conf Antimicrob Agents Chemother (Sept 28–Oct 1, New Orleans) 1986; Abst 939.
17. European Patent Appl. Publ. No. 132,116.
18. Sitrin R. D., Chan G. W., Chapin F., Giovenella A. J., Grappel S. F., Jeffs P. W., Phillips L., Snader K. M., and Nisbet L. J. Ardicins novel glycopeptide antibiotics. III. Preparation, Characterization and biological activities of aglycone derivatives. J. Antiblot. 1986; 39: 68–75.
19. European Patent Appl. Publ. No. 255,256.
20. Christensen, S. B., Allaudeen, H. S., Burke, M. R., Cart, S. A., Chung, S. K., DePhillips, P., Dingerdissen, J. J., DiPaolo, M., Giovenella, A. J., Heald, S. L., Killmer, L. B., Mico, B. A., Mueller, L., Pan, C. H., Poehland, B. L., Rake, J. B., Roberts, G. D., Shearer, M. C., Sitrin, R. D., Nisbet, L. J. and Jeffs, P. W. Parvodicin, a novel glycopeptide from a new species, Actinomadura parvosata: discovery, taxonomy, activity and structure elucidation, J Antiblot 1987; 40: 970–990.
21. Berdnikova, T. F., Tokareva, N. L., Abramova, E. A., Dokshina, N. Y., Potapova, N. P. and Lomakina, N. N. Structure of the aglycone of eremomycin, a novel antibiotic of the group of polycyclic glycopeptides. Antibiot Kimioter 1988; 33: 566–70.
22. Tsuji, N., Kobayashi, M., Kamigauchi, T., Yoshimura, Y. and Terui, Y. New glycopeptide antibiotics. I. The structures of orienticins. J Antibiot 1988; 41: 819–822.
23. European Patent Appln. Publ. No. 90578

24. U.S. Pat. No. 4,537,770
25. European Pat. Appln. Publ. No. 365 319
26. European Pat. Appln. Publ. No. 339 982
27. Folena-Wasserman, G., Poehland, L. B., Yeung, E. W-K., Staiger, D., Killmer, L. B., Snader, K., Dingerdissen, J. J. and Jeffs, P. W. Kibdelins (AAD-609), novel glycopeptide antibiotics. II. Isolation, purification, and structure. J Antibiot 1986; 39: 1395-1406.
28. European Pat. Appln. Publ. No. 100605
29. U.S. Pat. No. 4,029,769
30. Han, K. K., Tetaert, D., Debuire, B., Dantrevaux, M., Biserte, G. Dégradation récurrente d'Edman, Biochemie, 1977; 59:557-576
31. Nagarajan, R., and Schabel, A.A. Selective cleavage of vancosamine, glucose and N-methyl-leucine from vancomycin and related antibiotics. J. Chem. Soc. Comm.: 1988; 1306-1307.

We claim:

1. A process for producing a tetrapeptide of the general formula (Ic):

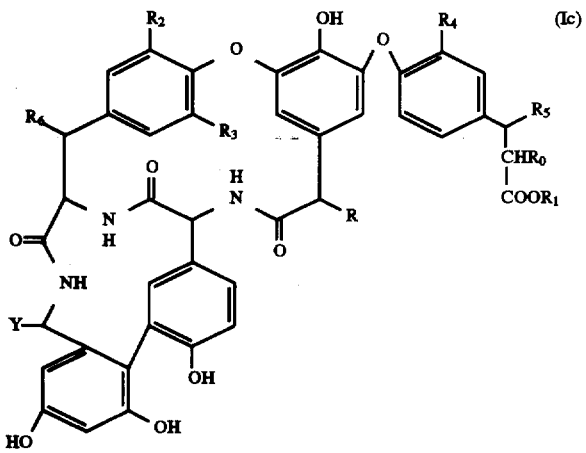

wherein:

R and $R_0$ each independently represent amino or a protected amino group;

$R_1$ represents hydrogen or a protecting group of the carboxylic function;

$R_2$ is hydrogen;

$R_3$ is hydrogen or chloro;

$R_4$ is hydrogen or chloro;

$R_5$ is hydrogen;

$R_6$ is hydrogen or hydroxy;

Y represents a carboxylic group or a functional derivative thereof, wherein said functional derivative is a carboxyester, a carboxamide or a substituted carboxamide; the phenolic hydroxy groups may optionally be protected; or its salts with acids and bases as well as its inner salts; which comprises:

i) selectively protecting the free amino groups and the phenolic hydroxy groups of a pentapeptide of the formula (IIIc);

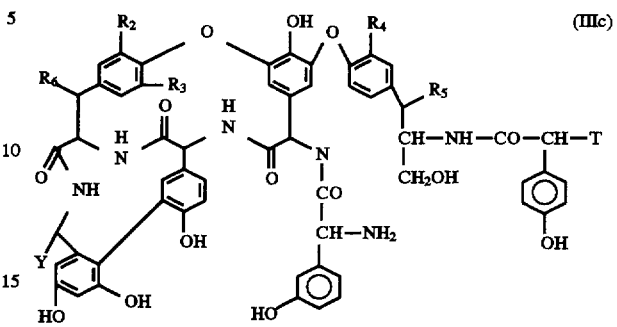

wherein:

T represent amino, alkylamino or a protected amino group from which the original amino group can be readily restored, and Y, $R_2$, $R_3$, $R_4$, $R_5$, and $R_6$ are as defined above, and its salts with acids and bases as well as its inner salts;

ii) oxidizing the hydroxymethyl moiety of the selectively protected pentapeptide to carboxy, yielding a compound of formula (IVc)

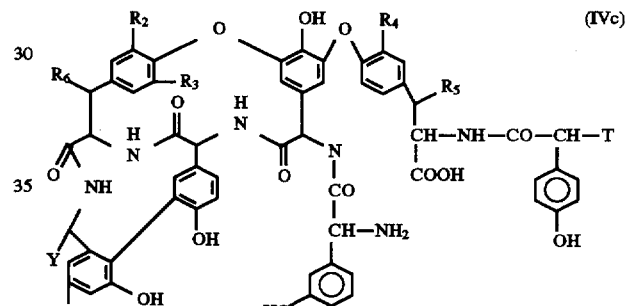

wherein T, Y, $R_2$, $R_3$, $R_4$, $R_5$ and $R_6$ have the same meanings as above;

iii) deprotecting the amino and, optionally, the phenolic hydroxy groups of the compound of formula (IVc), and;

iiii) submitting the above deprotected compound to a double Edman degradation and, optionally, protecting the free amino groups and the carboxylic rests of the resulting compound.

2. A process for producing a tetrapeptide of formula (Ic) of claim 1, which comprises:

i) submitting a pentapeptide compound of formula (IIIc) of claim 1

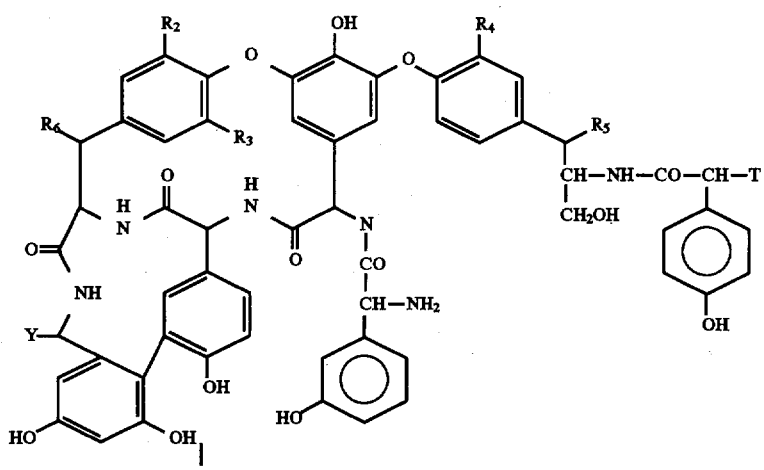

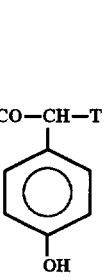 (IIIc)

wherein Y, $R_2$, $R_3$, $R_4$, $R_5$ and $R_6$ have the same meanings as in claim 1, to a double Edman degradation to yield a compound of formula (Vc)

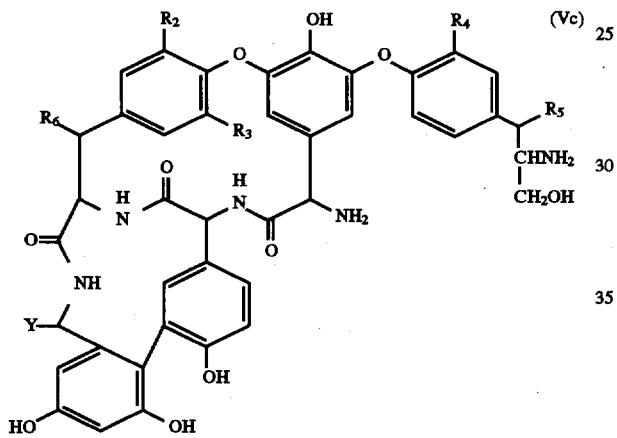

wherein Y, $R_2$, $R_3$, $R_4$, $R_5$ and $R_6$ have the same meanings as above;

ii) selectively protecting the free amino groups and the phenolic hydroxy groups of the compounds of formula (Vc);

iii) oxidizing the hydroxymethyl moiety of the selectively protected compound to carboxy and, optionally, deprotecting the amino and phenolic hydroxy groups of the resulting compound and;

iiii) optionally, transforming the compound of formula (Ic) wherein $R_1$ is hydrogen into the corresponding compound of formula (Ic) wherein $R_1$ is a protecting group of the carboxylic function.

* * * * *